US009771623B1

(12) United States Patent
Miller et al.

(10) Patent No.: US 9,771,623 B1
(45) Date of Patent: Sep. 26, 2017

(54) MOLECULAR TYPING SYSTEM FOR FLAVIVIRUS DIAGNOSTICS

(71) Applicants: Aaron L. Miller, Galveston, TX (US); Richard B. Pyles, Galveston, TX (US)

(72) Inventors: Aaron L. Miller, Galveston, TX (US); Richard B. Pyles, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/459,218

(22) Filed: Mar. 15, 2017

Related U.S. Application Data

(60) Provisional application No. 62/308,652, filed on Mar. 15, 2016.

(51) Int. Cl.
*C12Q 1/70* (2006.01)

(52) U.S. Cl.
CPC ....... *C12Q 1/701* (2013.01); *C12Q 2600/158* (2013.01)

(58) Field of Classification Search
CPC ........ A61K 39/12; A61K 38/162; C12N 7/00; C12N 2770/24121; C12N 2770/24221; C12N 2770/24111; C12N 2770/24151; C07K 14/005; G01N 33/56983; G01N 2333/185; G01N 2469/10
See application file for complete search history.

(56) References Cited

U.S. PATENT DOCUMENTS

| | | | | |
|---|---|---|---|---|
| 4,683,195 | A | 7/1987 | Mullis et al. | 435/6.11 |
| 4,683,202 | A | 7/1987 | Mullis | 435/91.2 |
| 4,786,600 | A | 11/1988 | Kramer et al. | 435/320.1 |
| 4,800,159 | A | 1/1989 | Mullis et al. | 435/91.2 |
| 5,422,252 | A | 6/1995 | Walker et al. | 435/91.2 |
| 2017/0014502 | A1* | 1/2017 | Sumathy | A61K 39/12 |

FOREIGN PATENT DOCUMENTS

| | | |
|---|---|---|
| EP | 0 320 308 | 6/1989 |
| WO | WO/90/14439 | 11/1990 |

OTHER PUBLICATIONS

Moureau et al, "A Real-Time RT-PCR Method for the Universal Detection and Identification of Flaviviruses," 2007, *Vector-Borne and Zoonotic Diseases*, vol. 7, No. 4, pp. 467-477.

* cited by examiner

*Primary Examiner* — Rachel B Gill
(74) *Attorney, Agent, or Firm* — Norton Rose Fulbright US LLP

(57) ABSTRACT

Certain embodiments of the invention include methods and compositions for evaluating flaviviruses, such as Zika virus, for the purpose of identifying, typing, and/or categorizing/speciation of virus in samples using nucleic acid sequencing.

16 Claims, 12 Drawing Sheets

```
CLUSTAL O(1.2.1) multiple sequence alignment

WNV_Clone_G1        TGTGTTTACAACATGATGGGAAAGAGAGAGAAAAAACCCGGAGAGTTCGGAAAGGCCAAG
Zika_Clone_A1       TGTGTGTACAACATGATGGGAAAAAGAGAAAAAAAACAAGGGGAATTTGGAAAGGCCAAG
DENV4_Clone_E2      TGT[redacted]TGAGAAAAAGTTAGGAGAGTTTGGCAGAGCCAAG
DENV2_Clone_C1      TGTGTGTATAACATGATGGGAAAAAGAGAGAAGAAGCTAGGGGAGTTCGGCAAGGCAAAA
DENV1_Clone_B1      TGTGTGTATAACATGATGGGAAAGAGAGAGAAAAAAATTAGGAGAGTTCGGAAAGGCAAAA
                    ***** ** **************  *  ** ** **    ** ** ** ** *  ** **

WNV_Clone_G1        GGAAGCAGAGCCATTTGGTTCATGTGGCTCGGAGCTCGCTTTCTGGAGTTCGAGGCTCTG
Zika_Clone_A1       GGCAGCCGCGCCATCTGGTACATGTGGCTAGGGGCTAGATTTCTAGAGTTCGAAGCCCTT
DENV4_Clone_E2      GGAAGCCGAGCAATC[redacted]CGCGGTTTCTGGAATTTGAAGCCCTG
DENV2_Clone_C1      GGTAGCAGAGCCATATGGTACATGTGGCTTGGAGCACGCTTCTTAGAGTTTGAAGCCCTA
DENV1_Clone_B1      GGAAGTCGCGCAATATGGTACATGTGGTTGGGAGCGCGCTTTTTAGAGCTTGAAGCCCTT
                    ** **  * ** ** **** ******* * ** **  * **  * **  * ** ** **

WNV_Clone_G1        GGTTTTCTCAATGAAGACCACTGGCTTGGAAGAAAGAACTCAGGAGGAGGTGTCGAGGGC
Zika_Clone_A1       GGATTCTTGAACGAGGATCACTGGATGGGGAGAGAGAATTCAGGAGGTGGTGTTGAAGGG
DENV4_Clone_E2      GGTTTTTTGAATGAAGATCACTGGTTTGGCAGAGAAAATTCATGGAGTGGAGTGGAAGGG
DENV2_Clone_C1      GGATTCTTGAATGAAGATCACTGGTTCTCCAGAGAGAACTCCTTGAGTGGAGTGGAAGGA
DENV1_Clone_B1      GGTTTCATGAATGAAGATCACTGGTTCAGCAGAGAGAATTCACTCAGTGGAGTGGAAGGA
                    ** **  * ** ** ** ****** *     *** * ** **      * ** ** ** **

WNV_Clone_G1        TTGGGCCTCAAAAAACTGGGTTACATCCTGCGTGAAGTTGGCACCCGGCCTGGGGGCAAG
Zika_Clone_A1       CTAGGATTACAAAGACTCGGATATGTCTTAGAAGAGATGAGTCGCATACCAGGAGGAAGG
DENV4_Clone_E2      GAAGGTCTGCACAGATTGGGATATATCCTGGAGGAGATAGACAAGAAGGATGGAGACCTA
DENV2_Clone_C1      GAAGGGCTGCACAAGCTAGGTTACATTTTAAGAGACGTGAGCAAGAAAGAGGGAGGAGCA
DENV1_Clone_B1      GAAGGACTCCACAAACTTGGATACATACTCAGAGACATATCAAAGATTCCAGGGGGAAAT
                       **  *  * *   * ** **  *  *    **  *              ** *

WNV_Clone_G1        ATCTATGCTGATGATACCGCCGGCTGGGACAC
Zika_Clone_A1       ATGTATGCAGATGATACCGCGGGCTGGGACAC
DENV4_Clone_E2      ATGTATGCCGATGACACCGCAGGCTGGGACAC
DENV2_Clone_C1      GTGTATGCCGATGACACAGCTGGCTGGGACAC
DENV1_Clone_B1      ATGTATGCAGATGACACCGCCGGCTGGGACAC
                     * ***** ***** ** ** ***********
```

FIG. 1

```
Cell_fusing_agent    CCAAGCCACATGTACCAGATGGTCCTTGAGCCCTTGGCCTCGCCAGCTAGGCTGGGCTTT
WNV                  CCGAGCCACATGAACCAAATGGCTCTGCTTCCCTTGGCCTTTCCGAACTCTCCGGGTTTT
Zika_IBH_30656       CCCAACCACATGTACCAGATTGCGCGGCTGCCTTTTGCTTTCCCGAATTCTCCTTGCTTC
Zika_DAK_41662       CCCAACCACATGTACCAGATTGCACGGCTGCCTTTTGCTTTCCCGAATTCTCCTTGCTTC
Zika_DAK_41671       CCCAACCACATGTACCAGATTGCGCGGCTGCCTTTTGCTTTCCCGAATTCTCCTTGCTTC
Zika_DAK_41525       CCCAACCACATGTACCAGATTGCGCGGCTGCCTTTTGCTTTCCCGAATTCTCCTTGCTTC
Zika_pb_7_Y0         CCTAGCCACATGTACCAAATGGCGCGGCTGCCCTTGGCCTTTCCAAATTCCCCTTGCTTC
Zika_1-7_EJA_Mex     CCTAGCCACATATACCAGATGGCGCGGCTGCCCTTGGCCTTTCCAAATTCCCCTTGTTTC
Zika_Asia            CCTAGCCACATGTACCAGATGGCGCGGCTGCCCTTGGCCTTTCCAAATTCCCCTTGTTTT
DENV3                CCCAACCACATGTACCATGTAGCCCTACTGCCTTTTGCTTTACCAAACTCTCCAAGTTTT
DENV4                CCCAGCCACATGTACCAGATTGCTCGGCTTCCCTTGGCTCTGCCAAACTCTCCTAACTTT
DENV1                CCCAACCACATGTACCATATTGCGCGACTTCCTTTTGCCTTTCCGAACTCTCCTAATTTT
DENV2                CCAAGCCACATGTACCATATGGCTCTGCTACCTTTTGCCTTGCCGAACTCCCCTAGCTTC
                     ** * ******  ****  * *  *     ** ** **    **       *     **
```

FIG. 2

| Sample | Virus Genus/Family | Flavi-seq |
|---|---|---|
| Alkhumra | Flavivirus | Alkhumra |
| CE TBE | Flavivirus | CE TBE |
| Cell fusing agent | Flavivirus | Cell fusing agent |
| Culex Flavi | Flavivirus - Mosquito-specific | Culex Flavi |
| DENV1 | Flavivirus | DENV1 |
| DENV2 | Flavivirus | DENV2 |
| DENV3 | Flavivirus | DENV3 |
| DENV4 | Flavivirus | DENV4 |
| Ilheus | Flavivirus | Ilheus |
| JEV | Flavivirus | JEV |
| Kamati River | Flavivirus | Kamati River |
| KFD | Flavivirus | KDF |
| Murray Valley Enc | Flavivirus | Murray Valley Enc |
| Nanay | Flavivirus | Nanay |
| Omsk | Flavivirus | Omsk |
| Powassan | Flavivirus | Powassan |
| RSSE | Flavivirus | RSSE |
| Spondweni | Flavivirus | Spondweni |
| St. Louis Enc | Flavivirus | St. Louis Enc |
| Usutu | Flavivirus | Usutu |
| WNV | Flavivirus | WNV |
| Yellow Fever Virus | Flavivirus | YFV |
| Zika -1-7 EJA Mex P/2 | Flavivirus | Zika |
| Zika - DAK A- 41525 D2-2 | Flavivirus | Zika |
| Zika - DAK A Ard 41662 D2-1 | Flavivirus | Zika |
| Zika - DAK Ar 41671 OG-1 | Flavivirus | Zika |
| Zika - FSS 13025 DG-3 | Flavivirus | Zika |
| Zika - IBH 30656 D5-3 | Flavivirus | Zika |
| Zika - pb-7 yo D7-1 | Flavivirus | Zika |
| Zika Cambodia | Flavivirus | Zika |
| Zika Mex-81 | Flavivirus | Zika |
| Zika Panama | Flavivirus | Zika |
| | | |
| Chikungunya | Alphavirus | |
| Mayaro | Alphavirus | |
| Onuong Nuong | Alphavirus | |
| HIV | Retroviridae | |
| genomic DNA | Control | |
| Serum | Control | |
| Urine | Control | |
| NTC | Control | |

FIG. 3

Assay: Flavi-seq from cDNA template

| Virus | Zika DAK 41525 | Zika 1-7 EJA Mex | DENV1 | DENV2 | DENV3 | DENV4 | Zika DAK 41525 | Zika 1-7 EJA Mex | DENV1 | DENV2 | DENV3 | DENV4 |
|---|---|---|---|---|---|---|---|---|---|---|---|---|
| Biofluid | Urine | Urine | Urine | Urine | Urine | Urine | Serum | Serum | Serum | Serum | Serum | Serum |
| Dilution | | | | | | | | | | | | |
| (1:1) | Zika | Zika | DENV1 | DENV2 | DENV3 | DENV4 | Zika | Zika | DENV1 | DENV2 | DENV3 | DENV4 |
| 1.00E-01 | Zika | Zika | DENV1 | DENV2 | DENV3 | DENV4 | Zika | Zika | DENV1 | DENV2 | DENV3 | DENV4 |
| 1.00E-02 | Zika | Zika | DENV1 | DENV2 | DENV3 | DENV4 | Zika | Zika | DENV1 | DENV2 | DENV3 | DENV4 |
| 1.00E-03 | Zika | Zika | DENV1 | DENV2 | DENV3 | DENV4 | Zika | Zika | DENV1 | DENV2 | DENV3 | DENV4 |
| 1.00E-04 | Zika | Zika | DENV1 | DENV2 | DENV3 | | Zika | Zika | DENV1 | DENV2 | DENV3 | DENV4 |
| 1.00E-05 | Zika | | DENV1 | DENV2 | DENV3 | DENV4 | Zika | | DENV1 | DENV2 | DENV3 | DENV4 |
| 1.00E-06 | Zika | | DENV1 | DENV2 | DENV3 | DENV4 | Zika | | DENV1 | DENV2 | DENV3 | DENV4 |
| Biofluid alone | | | | | | | | | | | | |

Assay: Pan-Flavi

| Virus | Zika DAK 41525 | Zika 1-7 EJA Mex | DENV1 | DENV2 | DENV3 | DENV4 | Zika DAK 41525 | Zika 1-7 EJA Mex | DENV1 | DENV2 | DENV3 | DENV4 |
|---|---|---|---|---|---|---|---|---|---|---|---|---|
| Biofluid | Urine | Urine | Urine | Urine | Urine | Urine | Serum | Serum | Serum | Serum | Serum | Serum |
| Dilution | | | | | | | | | | | | |
| (1:1) | 7.97E+06 | 8.15E+05 | 5.15E+08 | 1.89E+09 | 1.45E+09 | 1.09E+09 | 7.15E+06 | 9.17E+05 | 3.08E+08 | 4.79E+09 | 1.04E+09 | 1.45E+09 |
| 1.00E-01 | 8.88E+05 | 7.24E+04 | 3.60E+07 | 2.11E+08 | 2.12E+08 | 1.08E+08 | 1.03E+06 | 7.35E+04 | 2.14E+07 | 2.49E+08 | 1.78E+08 | 1.36E+08 |
| 1.00E-02 | 1.10E+05 | 9.12E+03 | 5.26E+06 | 3.25E+07 | 4.05E+07 | 1.50E+07 | 1.49E+05 | 1.24E+04 | 4.28E+06 | 3.90E+07 | 3.33E+07 | 1.97E+07 |
| 1.00E-03 | 1.55E+04 | 1.23E+03 | 6.15E+05 | 3.63E+06 | 5.25E+06 | 1.88E+06 | 2.63E+04 | 1.95E+03 | 6.13E+05 | 4.73E+06 | 4.85E+06 | 2.22E+06 |
| 1.00E-04 | 9.91E+02 | | 7.90E+04 | 5.61E+05 | 7.17E+05 | 3.15E+05 | 3.72E+03 | 1.95E+02 | 8.59E+04 | 8.33E+05 | 7.01E+05 | 3.83E+05 |
| 1.00E-05 | 9.63E+01 | | 1.60E+04 | 1.20E+05 | 1.53E+05 | 5.78E+04 | 7.74E+02 | | 1.19E+04 | 1.71E+05 | 1.65E+05 | 8.72E+04 |
| 1.00E-06 | | | 5.41E+02 | 1.83E+04 | 2.57E+04 | 8.67E+03 | 2.82E+01 | | 2.83E+03 | 2.95E+04 | 2.44E+04 | 1.00E+04 |
| Biofluid alone | | | | | | | | | | | | |

FIG. 5

Assay: Flavi-seq from cDNA template

| Virus | Zika DAK 41525 | Zika IBH30656 | Zika pb-7 Y0 | Zika FSS13025 | Zika 1-7 EJA Mex | Zika Mex-81 | Zika Panama | WNV | DENV1 | DENV2 | DENV3 | DENV4 |
|---|---|---|---|---|---|---|---|---|---|---|---|---|
| BioMatrix Mosquito | Mosquito | Mosquito | Mosquito | Mosquito | Mosquito | Mosquito | Mosquito | Mosquito | Mosquito | Mosquito | Mosquito | Mosquito |
| Dilution | | | | | | | | | | | | |
| | Zika | Zika | Zika | Zika | Zika | Zika | Zika | WNV | DENV1 | DENV2 | DENV3 | DENV4 |
| | Zika | Zika | Zika | Zika | Zika | Zika | Zika | WNV | DENV1 | DENV2 | DENV3 | DENV4 |
| | Zika | Zika | Zika | Zika | Zika | Zika | Zika | WNV | DENV1 | DENV2 | DENV3 | DENV4 |
| | Zika | Zika | Zika | Zika | | | | WNV | DENV1 | | DENV3 | DENV4 |
| | Zika | Zika | Zika | Zika | | | | WNV | DENV1 | | DENV3 | DENV4 |
| | Zika | | | | | | | | DENV1 | | DENV3 | |
| | | | | | | | | | | | DENV3 | |
| BioMatrix alone | | | | | | | | | | | | |

Assay: Pan-Flavi

| Virus | Zika DAK 41525 | Zika IBH30656 | Zika pb-7 Y0 | Zika FSS13025 | Zika 1-7 EJA Mex | Zika Mex-81 | Zika Panama | WNV | DENV1 | DENV2 | DENV3 | DENV4 |
|---|---|---|---|---|---|---|---|---|---|---|---|---|
| BioMatrix Mosquito | Mosquito | Mosquito | Mosquito | Mosquito | Mosquito | Mosquito | Mosquito | Mosquito | Mosquito | Mosquito | Mosquito | Mosquito |
| Dilution | | | | | | | | | | | | |
| 1.00E-01 | 1.48E+05 | 8.71E+05 | 1.63E+06 | 5.50E+05 | 1.35E+05 | 7.51E+05 | 1.02E+05 | 5.28E+06 | 7.08E+07 | 3.86E+08 | 4.07E+07 | 1.62E+08 |
| 1.00E-02 | 2.27E+04 | 8.36E+03 | 5.35E+04 | 8.06E+03 | 1.38E+03 | 9.77E+03 | 3.02E+03 | 8.51E+04 | 2.89E+06 | 6.64E+06 | 8.87E+05 | 9.76E+05 |
| 1.00E-03 | 3.01E+03 | 1.76E+03 | 5.06E+03 | 1.12E+03 | | | | 7.71E+03 | 2.20E+05 | 6.79E+05 | 8.97E+04 | 1.24E+05 |
| 1.00E-04 | 8.76E+02 | | 1.14E+03 | | | | | 1.07E+03 | 3.32E+04 | 6.34E+04 | 1.22E+04 | 2.76E+04 |
| 1.00E-05 | | | | | | | | | 2.82E+03 | 4.82E+03 | 1.23E+03 | 1.69E+03 |
| 1.00E-06 | | | | | | | | | | 1.35E+03 | | 4.08E+02 |
| 1.00E-07 | | | | | | | | | | | | |
| BioMatrix alone | | | | | | | | | | | | |

FIG. 6

| LOD (genome copies) | Flavi-seq (cDNA) | Flavi-seq (Nested) |
|---|---|---|
| Serum | 700 | BLD |
| Urine | 469 | BLD |
| Mosquito | 850 | N/A |

FIG. 7

| Clinical Sample Set - Bolivia/Colombia/Honduras | Zika qPCR (SQ) | Flavi-seq | Pyrosequence |
|---|---|---|---|
| 1 | | DENV1 | TATTGCACGACTTCCTTTTGCCTTTCCAACTCTCC |
| 2 | | DENV4 | GATTGCTCGGCTTCCCTTGGCTCTGCCAA |
| 3 | 1.47E+00 | Zika | GATGGCGCGGCTGCCCTTGGCCTTTCCAAATTCCCCTT |
| 4 | 2.50E+00 | Zika | GATGGCGCGGCTGCCCCTT |
| 5 | 2.97E+00 | Zika | GATGGCGCGGCTGCCCCTTGGCCTTCCAAATCCCCTTC |
| 6 | 3.91E+00 | Zika | GATGGCGCGGCTGCCCCTTGGCCCTTTTCCCC |
| 7 | 3.93E+00 | Zika | GATGGCGCGGCTGCCCTTGGCCTTTCCAAATTCCCCTTGTTTC |
| 8 | 4.59E+00 | Zika | GATGGCGCGGCTGCCCTTGGCCTTTCCAAATTCCCCTTGTTTC |
| 9 | 5.47E+00 | Zika | GATGGCGCGGCTGCCCTTGGCCTTTCCAAATTCCCCC |
| 10 | 5.93E+00 | Zika | GATGGCGCGGCTGCCCTTGGCCTTTCCAAATTCCCCTTGTTTC |
| 11 | 6.47E+00 | Zika | GATGGCGCGGCTGCCCTTGGCCTTTCCAAATTCCCCTT |
| 12 | 7.58E+00 | Zika | GATGGCGCGGCTGCCCTTGGCCTTTCCAAATTCCCCTTT |
| 13 | 8.73E+00 | Zika | GATGGCGCGGCTGCCCCTTGGCCTTTCCAAATTCCCCC |
| 14 | 1.86E+01 | Zika | GATGGCGCGGCTGCCCTTGGCCTTTTCCAAA |
| 15 | 1.86E+01 | Zika | GATGGCGCGGCTGCCCTTGGCCTTTCCCAAATTCCCCCTTT |
| 16 | 1.87E+01 | Zika | GATGGCGCGGCTGCCCAGGCCTTTCCAAATTCCCCTTGTTTC |
| 17 | 1.93E+01 | Zika | GATGGCGCGGCTGCCCTTGGCCTTTCCAAATTCCCCTTGTTTTC |
| 18 | 2.18E+01 | Zika | GATGGCGCGGCTGCCCTTGGCCTTTCCAATTCCCCTTGTTTC |
| 19 | 3.04E+01 | Zika | GATGGCGCGGCTGCCCTTGGCCTTTCCAAATTCCCCTTGTTTTC |
| 20 | 5.19E+01 | Zika | GATGGCGCGGCTGCCCCTTGGCCTTTCCAAATTCCCCTTGTTTC |
| 21 | 6.52E+01 | Zika | GATGGCGCGGCTGCCCTTGGCCTTTTCCAAA |
| 22 | 7.39E+01 | Zika | GATGGCGCGGCTGCCCTTGGCTTTTCCAAATTCCCCTT |
| 23 | 8.18E+01 | Zika | GATGGCGCGGCTGCCCTTGGCCTTTCCAAATTCCCCTTGTTTC |
| 24 | 9.47E+01 | Zika | GATGGCGCGGCTGCCCTTGGCCCAATTCCCCATTCC |
| 25 | 1.12E+02 | Zika | GATGGCGCGGCTGCCCTTGGCCTTTCCAAATTCCCCTTGTTTC |
| 26 | 1.78E+02 | Zika | GATGGCGCGGCTGCCCCTTGGCCCTTTCCAAA |
| 27 | 7.75E+03 | Zika | GATGGCGCGGCTGCCCTTGGCC |
| Positive molecular clone | 1.94E+07 | Zika | GATGGCGCGGCTGCCCTTGGCCTTTCCAAATTCCCCC |
| Negative | | | |

FIG. 8

| | Zika 835 | Zika 1086 | Zika 4481 | Zika 9271 | 12s | Flavi-seq | Pyrosequence |
|---|---|---|---|---|---|---|---|
| V00831 AEDES UTMB TEST ZIKA | | | | | 2.70E+06 | | |
| 3-14-16 V1080 | | | | | 6.10E+05 | | |
| 3-21-16 V1301 | | | | | 3.89E+05 | | |
| 3-21-16 V1253 | | | | | 5.91E+03 | | |
| 3-21-16 V1211 | | | | | 2.09E+04 | | |
| V00795 AEDES UTMB TEST ZIKA | | | | | 3.57E+03 | | |
| 3-14-16 V1089 | | | | | 3.81E+06 | | |
| 3-21-16 V1302 | | | | | 1.30E+05 | | |
| 3-21-16 V1254 | | | | | 3.61E+03 | | |
| 3-21-16 V1212 | | | | | 3.37E+04 | | |
| 3-7-16 V940 | | | | | 2.38E+06 | | |
| 3-14-16 V1095 | | | | | 3.13E+05 | | |
| 3-21-16 V1303 | | | | | 3.37E+04 | | |
| 3-21-16 V1255 | | | | | 2.82E+04 | | |
| 3-21-16 V1213 | | | | | 2.11E+04 | | |
| 3-7-16 V953 | | | | | 1.46E+07 | | |
| 3-14-16 V1129 | | | | | 3.87E+06 | | |
| 3-21-16 V1304 | | | | | 2.51E+04 | | |
| 3-21-16 V1256 | | | | | 4.10E+05 | | |
| 3-21-16 V1214 | | | | | 6.50E+04 | | |
| 3-7-16 V954 | | | | | 1.74E+06 | | |
| 3-21-16 V1333 | | | | | 4.10E+04 | | |
| 3-21-16 V1331 | | | | | 5.24E+03 | | |
| 3-21-16 V1268 | | | | | 4.51E+04 | | |
| 3-21-16 V1215 | | | | | 3.30E+04 | | |
| 3-7-16 V973 | | | | | 1.34E+07 | | |
| 3-21-16 V1271 | | | | | 1.19E+04 | | |
| 3-21-16 V1332 | | | | | 6.86E+04 | | |
| 3-21-16 V1269 | | | | | 2.31E+06 | Cell fusing agent virus | GATAGTCCTTGAGCCCCTTGGCCTCACCA |
| 3-21-16 V1216 | | | | | 8.44E+03 | | |
| 3-7-16 V999 | | | | | 1.10E+07 | | |
| 3-21-16 V1282 | | | | | 2.66E+05 | | |
| 3-21-16 V1251 | | | | | 4.51E+05 | | |
| 3-21-16 V1270 | | | | | 1.51E+05 | | |
| 3-21-16 V1237 | | | | | 8.05E+04 | | |
| 3-7-16 V1013 | | | | | 7.28E+06 | | |
| 3-21-16 V1300 | | | | | 2.75E+04 | | |
| 3-21-16 V1252 | | | | | 4.99E+05 | | |
| 3-21-16 V1210 | | | | | 3.38E+04 | | |
| 3-21-16 V1238 | | | | | 1.60E+06 | | |

FIG. 9

SEQUENCE LISTING

```
<160> NUMBER OF SEQ ID NOS: 63

<210> SEQ ID NO 1
<211> LENGTH: 272
<212> TYPE: DNA
<213> ORGANISM: West Nile virus
```

-continued

<400> SEQUENCE: 1
tgtgtttaca acatgatggg aaagagagag aaaaaacccg gagagttcgg aaaggccaag 60
ggaagcagag ccatttggtt catgtggctc ggagctcgct ttctggagtt cgaggctctg 120
ggttttctca atgaagacca ctggcttgga agaaagaact caggaggagg tgtcgagggc 180
ttgggcctca aaaaactggg ttacatcctg cgtgaagttg gcacccggcc tgggggcaag 240
atctatgctg atgataccgc cggctgggac ac 272

<210> SEQ ID NO 2
<211> LENGTH: 272
<212> TYPE: DNA
<213> ORGANISM: Artificial Sequence
<220> FEATURE:
<223> OTHER INFORMATION: Zika virus

<400> SEQUENCE: 2
tgtgtgtaca acatgatggg aaaaagagaa aaaaaacaag gggaatttgg aaaggccaag 60
ggcagccgcg ccatctggta catgtggcta ggggctagat ttctagagtt cgaagccctt 120
ggattcttga acgaggatca ctggatgggg agagagaatt caggaggtgg tgttgaaggg 180
ctaggattac aaagactcgg atatgtctta gaagagatga gtcgcatacc aggaggaagg 240
atgtatgcag atgataccgc gggctgggac ac 272

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
tgyrtbtaya acatgatggg 20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (9)..(9)
<223> OTHER INFORMATION: N is inosine
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 4
gtgtcccanc cngcngtrtc 20

<210> SEQ ID NO 5
<211> LENGTH: 25
<212> TYPE: DNA
<213> ORGANISM: Artificial Sequence
<220> FEATURE:
<223> OTHER INFORMATION: Synthetic Primer

<400> SEQUENCE: 5
gtgtctacaa catgatggga aagag 25

-continued

<210> SEQ ID NO 6
<211> LENGTH: 19
<212> TYPE: DNA
<213> ORGANISM: Artificial Sequence
<220> FEATURE:
<223> OTHER INFORMATION: Synthetic Primer

<400> SEQUENCE: 6
ctcccagcca catgtacca 19

<210> SEQ ID NO 7
<211> LENGTH: 16
<212> TYPE: DNA
<213> ORGANISM: Artificial Sequence
<220> FEATURE:
<223> OTHER INFORMATION: Synthetic Primer

<400> SEQUENCE: 7
ccagccacat gtacca 16

<210> SEQ ID NO 8
<211> LENGTH: 271
<212> TYPE: DNA
<213> ORGANISM: West Nile virus

<400> SEQUENCE: 8
tgtgtttaca acatgatggg aaagagagag aaaaacccgg agagttcgga aaggccaagg 60
gaagcagagc catttggttc atgtggctcg gagctcgctt tctggagttc gaggctctgg 120
gttttctcaa tgaagaccac tggcttggaa gaaagaactc aggaggaggt gtcgagggct 180
tgggcctcaa aaaactgggt tacatcctgc gtgaagttgg cacccggcct gggggcaaga 240
tctatgctga tgataccgcc ggctgggaca c 271

<210> SEQ ID NO 9
<211> LENGTH: 272
<212> TYPE: DNA
<213> ORGANISM: Artificial Sequence
<220> FEATURE:
<223> OTHER INFORMATION: Zika virus

<400> SEQUENCE: 9
tgtgtgtaca acatgatggg aaaaagagaa aaaaaacaag ggaatttgg aaaggccaag 60 ggcagccgcg ccatctggta catgtggcta ggggctagat ttctagagtt cgaagccctt 120
ggattcttga acgaggatca ctggatgggg agagagaatt caggaggtgg tgttgaaggg 180
ctaggattac aaagactcgg atatgtctta gaagagatga gtcgcatacc aggaggaagg 240
atgtatgcag atgataccgc gggctgggac ac 272

<210> SEQ ID NO 10
<211> LENGTH: 272
<212> TYPE: DNA
<213> ORGANISM: Dengue virus

<400> SEQUENCE: 10
tgtgtgtata acatgatggg aaaacgtgag aaaaagttag gagagtttgg cagagccaag 60
ggaagccgag caatctggta catgtggctg ggagcgcggt ttctggaatt tgaagccctc 120
ggttttttga atgaagatca ctggtttggc agagaaaatt catggagtgg agtggaaggg 180
gaaggtctgc acagattggg atatatcctg gaggagatag acaagaagga tggagaccta 240
atctatgccg atgacaccgc aggctgggac ac 272

<210> SEQ ID NO 11
<211> LENGTH: 272
<212> TYPE: DNA
<213> ORGANISM: Dengue virus

<400> SEQUENCE: 11
tgtgtgtata acatgatggg aaaaagagag aagaagctag gggagttcgg caaggcaaaa 60
ggtagcagag ccatatggta catgtggctt ggagcacgct tcttagagtt tgaagcccta 120
ggattcttga atgaagatca ctggttctcc agagagaact ccttgagtgg agtggaagga 180
gaagggctgc acaagctagg ttacatttta agagacgtga gcaagaaaga gggaggagca 240
gtgtatgccg atgacacagc tggctgggac ac 272

<210> SEQ ID NO 12
<211> LENGTH: 272
<212> TYPE: DNA
<213> ORGANISM: Dengue virus

<400> SEQUENCE: 12
tgtgtgtata acatgatggg aaagagagag aaaaaattag gagagttcgg aaaggcaaaa 60
ggaagtcgcg caatatggta catgtggttg ggagcgcgct ttttagagct tgaagccctt 120
ggtttcatga atgaagatca ctggttcagc agagagaatt cactcagtgg agtggaagga 180
gaaggactcc acaaacttgg atacatactc agagacatat caaagattcc agggggaaat 240
atgtatgcag atgacaccgc cggctgggac ac 272

<210> SEQ ID NO 13
<211> LENGTH: 60
<212> TYPE: DNA
<213> ORGANISM: Artificial Sequence
<220> FEATURE:
<223> OTHER INFORMATION: Synthetic Primer

<400> SEQUENCE: 13
ccaagccaca tgtaccagat ggtccttgag cccttggcct cgccagctag gctgggcttt 60

<210> SEQ ID NO 14
<211> LENGTH: 60
<212> TYPE: DNA
<213> ORGANISM: Artificial Sequence
<220> FEATURE:
<223> OTHER INFORMATION: Synthetic Primer

<400> SEQUENCE: 14
ccgagccaca tgaaccaaat ggctctgctt cccttggcct ttccgaactc tccgggtttt 60

<210> SEQ ID NO 15
<211> LENGTH: 60
<212> TYPE: DNA
<213> ORGANISM: Artificial Sequence
<220> FEATURE:
<223> OTHER INFORMATION: Zika virus

<400> SEQUENCE: 15
cccaaccaca tgtaccagat tgcgcggctg ccttttgctt tcccgaattc tccttgcttc 60

<210> SEQ ID NO 16
<211> LENGTH: 60
<212> TYPE: DNA
<213> ORGANISM: Artificial Sequence
<220> FEATURE:
<223> OTHER INFORMATION: Zika virus

<400> SEQUENCE: 16
cccaaccaca tgtaccagat tgcacggctg ccttttgctt tcccgaattc tccttgcttc 60

<210> SEQ ID NO 17
<211> LENGTH: 60
<212> TYPE: DNA
<213> ORGANISM: Artificial Sequence
<220> FEATURE:
<223> OTHER INFORMATION: Zika virus

<400> SEQUENCE: 17
cccaaccaca tgtaccagat tgcgcggctg ccttttgctt tcccgaattc tccttgcttc 60

<210> SEQ ID NO 18
<211> LENGTH: 60
<212> TYPE: DNA
<213> ORGANISM: Artificial Sequence
<220> FEATURE:
<223> OTHER INFORMATION: Zika virus

<400> SEQUENCE: 18
cccaaccaca tgtaccagat tgcgcggctg ccttttgctt tcccgaattc tccttgcttc 60

<210> SEQ ID NO 19
<211> LENGTH: 60
<212> TYPE: DNA
<213> ORGANISM: Artificial Sequence
<220> FEATURE:
<223> OTHER INFORMATION: Zika virus

<400> SEQUENCE: 19
cctagccaca tgtaccaaat ggcgcggctg cccttggcct ttccaaattc cccttgcttc 60

<210> SEQ ID NO 20
<211> LENGTH: 60
<212> TYPE: DNA
<213> ORGANISM: Artificial Sequence
<220> FEATURE:
<223> OTHER INFORMATION: Zika virus

<400> SEQUENCE: 20
cctagccaca tataccagat ggcgcggctg cccttggcct ttccaaattc cccttgtttc 60

<210> SEQ ID NO 21
<211> LENGTH: 60
<212> TYPE: DNA
<213> ORGANISM: Artificial Sequence
<220> FEATURE:
<223> OTHER INFORMATION: Zika virus

<400> SEQUENCE: 21
cctagccaca tgtaccagat ggcgcggctg cccttggcct ttccaaattc cccttgtttt 60

<210> SEQ ID NO 22
<211> LENGTH: 60
<212> TYPE: DNA
<213> ORGANISM: Dengue virus

<400> SEQUENCE: 22
cccaaccaca tgtaccatgt agccctactg ccttttgctt taccaaactc tccaagtttt 60

<210> SEQ ID NO 23
<211> LENGTH: 60
<212> TYPE: DNA
<213> ORGANISM: Dengue virus

<400> SEQUENCE: 23
cccagccaca tgtaccagat tgctcggctt cccttggctc tgccaaactc tcctaacttt 60

<210> SEQ ID NO 24
<211> LENGTH: 60
<212> TYPE: DNA
<213> ORGANISM: Dengue virus

<400> SEQUENCE: 24
cccaaccaca tgtaccatat tgcgcgactt ccttttgcct ttccgaactc tcctaatttt 60

<210> SEQ ID NO 25
<211> LENGTH: 60
<212> TYPE: DNA
<213> ORGANISM: Dengue virus

<400> SEQUENCE: 25
ccaagccaca tgtaccatat ggctctgcta ccttttgcct tgccgaactc ccctagcttc 60

<210> SEQ ID NO 26
<211> LENGTH: 40
<212> TYPE: DNA
<213> ORGANISM: Artificial Sequence
<220> FEATURE:
<223> OTHER INFORMATION: Synthetic Primer

<400> SEQUENCE: 26
gatggcgcgg ctgcccttgg cctttccaaa ttcccccttt 40

<210> SEQ ID NO 27
<211> LENGTH: 30
<212> TYPE: DNA
<213> ORGANISM: Artificial Sequence
<220> FEATURE:
<223> OTHER INFORMATION: Synthetic Primer

<400> SEQUENCE: 27
gatggcgcgg ctgcccttgg cctttccaaa 30

<210> SEQ ID NO 28
<211> LENGTH: 36
<212> TYPE: DNA
<213> ORGANISM: Artificial Sequence
<220> FEATURE:
<223> OTHER INFORMATION: Synthetic Primer

<400> SEQUENCE: 28
gatggcgcgg ctgcccttgg cctttccaaa ttcccc 36

<210> SEQ ID NO 29
<211> LENGTH: 36
<212> TYPE: DNA
<213> ORGANISM: Artificial Sequence
<220> FEATURE:
<223> OTHER INFORMATION: Synthetic Primer

<400> SEQUENCE: 29
aatggcgcgg ctgcccttgg cctttccaaa ttcccc 36

<210> SEQ ID NO 30
<211> LENGTH: 36
<212> TYPE: DNA
<213> ORGANISM: Artificial Sequence
<220> FEATURE:
<223> OTHER INFORMATION: Synthetic Primer -continued

<400> SEQUENCE: 30
aatggctctg cttcccttgg cctttccgaa ctctcc 36

<210> SEQ ID NO 31
<211> LENGTH: 36
<212> TYPE: DNA
<213> ORGANISM: Artificial Sequence
<220> FEATURE:
<223> OTHER INFORMATION: Synthetic Primer

<400> SEQUENCE: 31
tattgcgcga cttccttttg cctttccgaa ctctcc 36

<210> SEQ ID NO 32
<211> LENGTH: 27
<212> TYPE: DNA
<213> ORGANISM: Artificial Sequence
<220> FEATURE:
<223> OTHER INFORMATION: Synthetic Primer

<400> SEQUENCE: 32
tatggctctg ctaccttttg ccttgcc 27

<210> SEQ ID NO 33
<211> LENGTH: 24
<212> TYPE: DNA
<213> ORGANISM: Artificial Sequence
<220> FEATURE:
<223> OTHER INFORMATION: Synthetic Primer

<400> SEQUENCE: 33
tatagctcta ctgccttttg cttt 24

<210> SEQ ID NO 34
<211> LENGTH: 33
<212> TYPE: DNA
<213> ORGANISM: Artificial Sequence
<220> FEATURE:
<223> OTHER INFORMATION: Synthetic Primer

<400> SEQUENCE: 34
gattgctcgg cttcccttgg ctctgccaaa ctc 33

<210> SEQ ID NO 35
<211> LENGTH: 35
<212> TYPE: DNA
<213> ORGANISM: Dengue virus

<400> SEQUENCE: 35
tattgcacga cttccttttg cctttccaac tctcc 35

<210> SEQ ID NO 36
<211> LENGTH: 29
<212> TYPE: DNA
<213> ORGANISM: Dengue virus

<400> SEQUENCE: 36
gattgctcgg cttcccttgg ctctgccaa 29

<210> SEQ ID NO 37
<211> LENGTH: 38
<212> TYPE: DNA
<213> ORGANISM: Artificial Sequence
<220> FEATURE:
<223> OTHER INFORMATION: Zika virus

<400> SEQUENCE: 37
gatggcgcgg ctgcccttgg cctttccaaa ttcccctt 38

<210> SEQ ID NO 38
<211> LENGTH: 19
<212> TYPE: DNA
<213> ORGANISM: Artificial Sequence
<220> FEATURE:
<223> OTHER INFORMATION: Zika virus

<400> SEQUENCE: 38
gatggcgcgg ctgcccctt 19

<210> SEQ ID NO 39
<211> LENGTH: 38
<212> TYPE: DNA
<213> ORGANISM: Artificial Sequence
<220> FEATURE:
<223> OTHER INFORMATION: Zika virus

<400> SEQUENCE: 39
gatggcgcgg ctgccccttg gccttccaaa tccccttc 38

<210> SEQ ID NO 40
<211> LENGTH: 32
<212> TYPE: DNA
<213> ORGANISM: Artificial Sequence
<220> FEATURE:
<223> OTHER INFORMATION: Zika virus

<400> SEQUENCE: 40
gatggcgcgg ctgccccttg gcccttttcc cc 32

<210> SEQ ID NO 41
<211> LENGTH: 43
<212> TYPE: DNA
<213> ORGANISM: Artificial Sequence
<220> FEATURE:
<223> OTHER INFORMATION: Zika virus

<400> SEQUENCE: 41
gatggcgcgg ctgcccttgg cctttccaaa ttccccttgt ttc 43

<210> SEQ ID NO 42
<211> LENGTH: 43
<212> TYPE: DNA
<213> ORGANISM: Artificial Sequence
<220> FEATURE:
<223> OTHER INFORMATION: Zika virus

<400> SEQUENCE: 42
gatggcgcgg ctgcccttgg cctttccaaa ttccccttgt ttc 43

<210> SEQ ID NO 43
<211> LENGTH: 37
<212> TYPE: DNA
<213> ORGANISM: Artificial Sequence
<220> FEATURE:
<223> OTHER INFORMATION: Zika virus

<400> SEQUENCE: 43
gatggcgcgg ctgcccttgg cctttccaaa ttccccc 37

<210> SEQ ID NO 44
<211> LENGTH: 43
<212> TYPE: DNA
<213> ORGANISM: Artificial Sequence
<220> FEATURE:
<223> OTHER INFORMATION: Zika virus

<400> SEQUENCE: 44
gatggcgcgg ctgcccttgg cctttccaaa ttccccttgt ttc         43

<210> SEQ ID NO 45
<211> LENGTH: 38
<212> TYPE: DNA
<213> ORGANISM: Artificial Sequence
<220> FEATURE:
<223> OTHER INFORMATION: Zika virus

<400> SEQUENCE: 45
gatggcgcgg ctgcccttgg cctttccaaa ttcccctt              38

<210> SEQ ID NO 46
<211> LENGTH: 39
<212> TYPE: DNA
<213> ORGANISM: Artificial Sequence
<220> FEATURE:
<223> OTHER INFORMATION: Zika virus

<400> SEQUENCE: 46
gatggcgcgg ctgcccttgg cctttccaaa ttccccttt             39

<210> SEQ ID NO 47
<211> LENGTH: 38
<212> TYPE: DNA
<213> ORGANISM: Artificial Sequence
<220> FEATURE:
<223> OTHER INFORMATION: Zika virus

<400> SEQUENCE: 47
gatggcgcgg ctgcccccttg gcctttccaa attccccc             38

<210> SEQ ID NO 48
<211> LENGTH: 31
<212> TYPE: DNA
<213> ORGANISM: Artificial Sequence
<220> FEATURE:
<223> OTHER INFORMATION: Zika virus

<400> SEQUENCE: 48
gatggcgcgg ctgcccttgg ccttttccaa a                     31

<210> SEQ ID NO 49
<211> LENGTH: 41
<212> TYPE: DNA
<213> ORGANISM: Artificial Sequence
<220> FEATURE:
<223> OTHER INFORMATION: Zika virus

<400> SEQUENCE: 49
gatggcgcgg ctgcccttgg cctttcccaa attccccctt t          41

<210> SEQ ID NO 50
<211> LENGTH: 42
<212> TYPE: DNA
<213> ORGANISM: Artificial Sequence
<220> FEATURE:
<223> OTHER INFORMATION: Zika virus

<400> SEQUENCE: 50
gatggcgcgg ctgcccaggc ctttccaaat tccccttgtt tc 42

<210> SEQ ID NO 51
<211> LENGTH: 44
<212> TYPE: DNA
<213> ORGANISM: Artificial Sequence
<220> FEATURE:
<223> OTHER INFORMATION: Zika virus

<400> SEQUENCE: 51
gatggcgcgg ctgcccttgg cctttccaaa ttccccttgt tttc 44

<210> SEQ ID NO 52
<211> LENGTH: 42
<212> TYPE: DNA
<213> ORGANISM: Artificial Sequence
<220> FEATURE:
<223> OTHER INFORMATION: Zika virus

<400> SEQUENCE: 52
gatggcgcgg ctgcccttgg cctttccaat tccccttgtt tc 42

<210> SEQ ID NO 53
<211> LENGTH: 44
<212> TYPE: DNA
<213> ORGANISM: Artificial Sequence
<220> FEATURE:
<223> OTHER INFORMATION: Zika virus

<400> SEQUENCE: 53
gatggcgcgg ctgcccttgg cctttccaaa ttccccttgt tttc 44

<210> SEQ ID NO 54
<211> LENGTH: 44
<212> TYPE: DNA
<213> ORGANISM: Artificial Sequence
<220> FEATURE:
<223> OTHER INFORMATION: Zika virus

<400> SEQUENCE: 54
gatggcgcgg ctgcccccttg gcctttccaa attccccttg tttc 44

<210> SEQ ID NO 55
<211> LENGTH: 31
<212> TYPE: DNA
<213> ORGANISM: Artificial Sequence
<220> FEATURE:
<223> OTHER INFORMATION: Zika virus

<400> SEQUENCE: 55
gatggcgcgg ctgcccttgg ccttttccaa a 31

<210> SEQ ID NO 56
<211> LENGTH: 38
<212> TYPE: DNA
<213> ORGANISM: Artificial Sequence
<220> FEATURE:
<223> OTHER INFORMATION: Zika virus

<400> SEQUENCE: 56
gatggcgcgg ctgcccttgg cttttccaaa ttcccctt 38

-continued

<210> SEQ ID NO 57
<211> LENGTH: 43
<212> TYPE: DNA
<213> ORGANISM: Artificial Sequence
<220> FEATURE:
<223> OTHER INFORMATION: Zika virus

<400> SEQUENCE: 57
gatggcgcgg ctgcccttgg cctttccaaa ttccccttgt ttc 43

<210> SEQ ID NO 58
<211> LENGTH: 36
<212> TYPE: DNA
<213> ORGANISM: Artificial Sequence
<220> FEATURE:
<223> OTHER INFORMATION: Zika virus

<400> SEQUENCE: 58
gatggcgcgg ctgcccttgg cccaattccc cattcc 36

<210> SEQ ID NO 59
<211> LENGTH: 43
<212> TYPE: DNA
<213> ORGANISM: Artificial Sequence
<220> FEATURE:
<223> OTHER INFORMATION: Zika virus

<400> SEQUENCE: 59
gatggcgcgg ctgcccttgg cctttccaaa ttccccttgt ttc 43

<210> SEQ ID NO 60
<211> LENGTH: 32
<212> TYPE: DNA
<213> ORGANISM: Artificial Sequence
<220> FEATURE:
<223> OTHER INFORMATION: Zika virus

<400> SEQUENCE: 60
gatggcgcgg ctgccccttg gccctttcca aa 32

<210> SEQ ID NO 61
<211> LENGTH: 22
<212> TYPE: DNA
<213> ORGANISM: Artificial Sequence
<220> FEATURE:
<223> OTHER INFORMATION: Zika virus

<400> SEQUENCE: 61
gatggcgcgg ctgcccttgg cc 22

<210> SEQ ID NO 62
<211> LENGTH: 37
<212> TYPE: DNA
<213> ORGANISM: Artificial Sequence
<220> FEATURE:
<223> OTHER INFORMATION: Zika virus

<400> SEQUENCE: 62
gatggcgcgg ctgcccttgg cctttccaaa ttccccc 37

<210> SEQ ID NO 63
<211> LENGTH: 29
<212> TYPE: DNA
<213> ORGANISM: Artificial Sequence
<220> FEATURE:
<223> OTHER INFORMATION: Synthetic Primer -continued
<400> SEQUENCE: 63
gatagtcctt gagccccttg gcctcacca 29

MOLECULAR TYPING SYSTEM FOR FLAVIVIRUS DIAGNOSTICS

PRIORITY CLAIM

The present application claims priority to U.S. Application No. 62/308,652 filed Mar. 15, 2016, which is incorporated herein by reference in its entirety.

SUMMARY

Embodiments of the invention address serious issues in both diagnostic and epidemiological studies of flavivirus infections in children and adults. Sensitive and accurate diagnostic testing is crucial for early viral detection as evidenced by the recent Zika epidemics and associated impacts upon fetal development and viability. Because Flaviviridae share a high degree of sequence similarity and are prone to base changes that negate primer binding for commonly targeted viral genes currently recommended qPCR assays for specific family members (e.g., Zika) often result in cross-priming leading to misidentification (false positives) of the virus present in the clinical material. Further, the loss of specific sequence leads to a lack of detection and misdiagnosis (false negatives). This is exemplified by Zika, which creates grave concerns for pregnancy outcomes that is often misdiagnosed or missed due to the divergence of genetic lineages that are not recognized by the CDC recommended assays. Misdiagnosis is also an issue for other members of the Flaviviridae genus that can cause similar symptomology making improved molecular diagnoses critical to improving human health and properly monitoring the dissemination of the infections by insects that are evaluated through molecular sentineling programs. Finally, it is almost impossible to successfully identify co-infected materials that carry two members from this virus family by qPCR methods; this is a common outcome due to the geographical distribution of the viruses in the genus and the mosquito or tick vector. This complication is also a concern for the insect vector sentinel programs to show the spreading distribution of the virus across the planet.

Sensitive and specific diagnosis of flavivirus infections is a crucial consideration for at risk patients. Current literature describes the many failings of the current assays including unacceptably high false positive and negative rates. Aspects of the current invention addresses both of these issues through nested amplification of a broadly conserved region of the family of flaviviruses including family members often misdiagnosed as Zika. Aspects of the invention described herein accurately and specifically discriminates among members of the Flaviviridae family confirming the identification of the correct virus adding a further degree of confidence beyond positive qPCR results currently being utilized. Identification of mixed sample populations also can be identified with the described assays.

Certain embodiments of the invention include, but are not limited to PCR primer pairs, sequencing primers, and/or associated thermocycling protocols and kits targeting a region in the flavivirus NS5 coding region or gene for the purpose of identifying, subtyping, and/or classifying of virus in samples using nucleic acid sequencing. The sequencing procedures can use nucleic acid templates, such as cDNA or PCR amplicons, as a template for sequencing in medium to high throughput format that is cost effective and easily deployed to other clinical microbiology laboratories.

Certain embodiments are directed to an isolated flavivirus nucleic acid segment of 55, 60, 65, 70, 75, 80, 85, or 90 nucleotides to 70, 75, 80, 85, 90, 100, 125, 150, 175, 200, 225, 250, 275, 280 nucleotides in length, including all values and ranges there between, of a flavivirus, such as a Zika virus. In certain aspects a first target region is amplified using (i) a forward primer having a nucleotide sequence comprising or consisting of TGYRTBTAYAACATGATGGG (SEQ ID NO:3) and (ii) a reverse primer having a nucleotide sequence comprising or consisting of GTGTCCCAICCNGCNGTRTC (SEQ ID NO:4), where Y designates a C or T(U), K designates a G or T(U), M designates an A or C, S designates a G or C, R designates an A or G, and I is inosine, producing a first amplicon. In certain aspects a second target region is amplified using (i) a forward primer having a nucleotide sequence comprising or consisting of GTGTCTACAACATGATGGGAAAGAG (SEQ ID NO:5) and (ii) a reverse primer having a nucleotide sequence comprising or consisting of CTCCCAGCCACATGTACCA (SEQ ID NO:6) producing a second target region or a nested amplicon. In certain aspects the nested amplicon can be sequenced using an optimized sequencing primer comprising or consisting of CCAGCCACATGTACCA (SEQ ID NO:7).

In certain embodiments the first target region or amplicon consists of or corresponds to a West Nile target region having or consisting of the nucleotide sequence TGTGTTTACAACATGATGGGAAAGAGAGAGAAAAAACCCGGAGAGTTCGGAAAGGCCAAGGGAAGCAGAGCCATTTGGTTCATGTGGCTCGGAGCTCGCTTTCTGGAGTTCGAGGCTCTGGGTTTTCTCAATGAAGACCACTGGCTTGGAAGAAAGAACTCAGGAGGAGGTGTCGAGGGCTTGGGCCTCAAAAAACTGGGTTACATCCTGCGTGAAGTTGGCACCCGGCCTGGGGGCAAGATCTATGCTGATGATACCGCCGGCTGGGACAC (SEQ ID NO:1) or to a Zika virus target region having or consisting of the nucleotide sequence TGTGTGTACCAACATGATGGGAAAAAGAGAAAAAAAACAAGGGGAATTTGGAAAGGCCAAGGGCAGCCGCGCCATCTGGTACATGTGGCTAGGGGCTAGATTTCTAGAGTTCGAAGCCCTTGGATTCTTGAACGAGGATCACTGATGGGGAGAGAGAATTCAGGAGGTGGTGTTGAAGGGCTAGGATTACAAAGACTCGGATATGTCTTAGAAGAGATGAGTCGCATACCAGGAGGAAGGATGTATGCAGATGATACCGCGGGCTGGGACAC (SEQ ID NO: 2)—amplimer and sequence primer regions are underlined.

In a further aspect a second target region or amplicon corresponds to a target region from West Nile virus having or consisting of the nucleotide sequence of GTTTACAACATGATGGGAAAGAGAGAGAAAAAACCCGGAGAGTTCGGAAAGGCCAAGGGAAGCAGAGCCATTTGGTTCATGTGGCTCGGAG (nucleotides 3 to 94 of SEQ ID NO:1) or Zika virus target region having or consisting of the nucleotide sequence GTGTACAACATGATGGGAAAAAGAGAAAAGAAACAAGGGGAATTTGGAAAGGCCAAGGGCAGCCGCGCCATCTGGTAATGTGGCTAGGGG (nucleotides 3 to 94 of SEQ ID NO: 2). The term "correspond" or "corresponding sequence" refers to a nucleic acid segment that can be identified by sequence similarity and/or location within a viral genome. The corresponding sequences can be aligned or analyzed and the sequence difference(s) between two or more corresponding or analogous sequences can be determined. In certain aspects the sequence is used to identify a flavivirus present in a sample. A corresponding or analogous sequence will have a sequence identity of 70, 75, 80, 85, 90, 95, or 100% over the length of corresponding segment. The nucleic acid segment can be a flavivirus nucleic acid segment, such as a Zika virus nucleic acid segment. In a further aspect, the isolated nucleic acid segment is single or double stranded. In certain aspects the isolated nucleic acid segment comprises or consist of a flavivirus nucleic acid sequence corresponding to SEQ ID NO:1 or 2, or the complement of SEQ ID NO:1 or 2. The sequence listing implicitly discloses the complement of any polynucleotide provided.

In certain aspects one or both strands of a nucleic acid segment can be coupled to the same or different affinity agents, which includes but is not limited to, biotin, fucose, dinitrophenyl (DNP), metal or metal cluster, and the like. As used herein, the term "affinity agent" refers to any of a variety of compounds that can be incorporated into or coupled to a nucleic acid and which can selectively bind a "binding agent", thus allowing for immobilization of the nucleic acid bearing the affinity agent—biotin/streptavidin is an example of an affinity agent/binding agent pair. Binding agents can be coupled or attached to other supports or surfaces such as metal or polymeric supports or surfaces, or metal or polymeric beads or chips.

Certain embodiments are directed to an oligonucleotide or an oligonucleotide primer. Such primers can be used to isolate, amplify, and/or analyze a nucleic acid segment described herein. In certain aspects one, two, or more first oligonucleotide primers of 16, 17, 18, 19, 20, 21, 22, 23, 24, 25, 26, 27, 28, 29, or 30 nucleotides, including all values and ranges there between, comprises or consists of a nucleotide sequence that is at least 70, 75, 80, 85, 90, 95 or 100% identical to or consisting of TGYRTBTAYAACATGATGGG (SEQ ID NO:3); GTGTCCCAICCNGCNGTRTC (SEQ ID NO:4); GTGTCTACAACATGATGGGAAAGAG (SEQ ID NO:5); CTCCCAGCCACATGTACCA (SEQ ID NO:6); and/or CCAGCCACATGTACCA (SEQ ID NO:7)—where Y designates a C or T(U), K designates a G or T(U), M designates an A or C, S designates a G or C, R designates an A or G, and I is inosine, producing a first amplicon. In still a further aspect one or more of the oligonucleotide primers are coupled to an affinity agent. In certain aspects a first oligonucleotide primer consist of the nucleotide sequence of SEQ ID NO:3, 4, 5, or 6. In certain aspects two or more of the oligonucleotide primers are provided in an amplification mixture or kit. In certain aspects the kit is a flavivirus profiling kit.

Certain embodiments are directed to a kit comprising two or more oligonucleotide primers as described herein. In certain aspects the kit further comprises an oligonucleotide or oligonucleotide mixture comprising or consisting of one or more of TGYRTBTAYAACATGATGGG (SEQ ID NO:3); GTGTCCCAICCNGCNGTRTC (SEQ ID NO:4); GTGTCTACAACATGATGGGAAAGAG (SEQ ID NO:5); CTCCCAGCCACATGTACCA (SEQ ID NO:6); and/or CCAGCCACATGTACCA (SEQ ID NO:7). In certain aspects the primer of SEQ ID NO:7 is a sequencing primer. In certain aspects the kit comprising the appropriate reagents and flavivirus controls.

Certain embodiments are directed to methods of identifying or profiling flavivirus in a sample, detecting the presence of and identifying one or more flavivirus in a sample. In a certain aspects a plurality of flavivirus are identified in a single sample. In a further aspect the sample is a pool of insect vectors or a sentinel sample, e.g., mosquitoes or ticks. The pool can be characterized by identifying one or more flavivirus contained in the pool. In certain aspects one or more flaviviruses are identified by sequencing. In a further aspect the one or more flaviviruses are identified from a single target amplification reaction, e.g., a pool of second target regions are amplified and identified by sequencing, as described herein. In certain aspects the sample is suspected of or at risk of comprising a flavivirus such as West Nile, Dengue, St. Louis encephalitis virus, Zika virus, and the like. The methods can comprise isolating a nucleic acid segment of a flavivirus or Zika virus comprising a nucleic acid segment corresponding or analogous to a nucleic acid segment of SEQ ID NO:1 or 2, wherein the isolated nucleic acid has a length of 50, 55, 60, 65, 70, 75, 80, 90, 95, 100, 105, 110, 115, 120, 125 nucleotides to 100, 105, 110, 115, 120, 125, 150, 155, 160, 165, 170, 175, 200, up to 500 nucleotides, including all values and ranges there between. In certain aspects the first amplicon can be 250 to 280 nucleotides and the second or nested amplicon can be 70 to 110 nucleotides. In a further aspect the first amplicon is or is about 269 nucleotides and the second amplicon is or is about 91 nucleotides. In certain aspects the methods include determining the nucleotide sequence of the isolated nucleic acid segment, wherein the nucleotide sequence identifies the flavivirus(es), such as a Zika virus, in the sample. In certain aspects more than 1, 2, 3, 4, 5 or more flavivirus are present in a sample. In a further aspect a plurality of isolated nucleic acid segments are isolated and/or sequenced. In still a further aspect the isolated nucleic acid is an amplicon, such as, but not limited to a PCR amplicon. In further aspects the nucleotide sequence is determined by pyrosequencing. The sample can be a biological sample. In certain aspects the biological sample can be from an insect, human, or animal. In certain aspects the sample is an insect sample. In a further aspect the biological sample can be an insect(s), a tissue sample or homogenate, seminal fluid, amniotic fluid, blood, sera, urine, lymph, sputum, saliva, or other biological material that can harbor a flavivirus. In certain aspects the sample is a urine sample.

As used herein the terms "specific to" or "specific for" a target sequence, in relation to a nucleic acid sequence such as an oligonucleotide sequence, relate to a nucleotide sequence that hybridizes or anneals, under conditions used in given circumstances (e.g., temperature, salt concentration, etc.), to the target but does not hybridize under those circumstances to sequences that are not target sequences providing specificity of hybridization or annealing. Nucleotide sequences that are specific for a particular target or group of targets, such as a flavivirus and/or a Zika virus target sequences, are contemplated. Oligonucleotides specific to or specific for a flavivirus and/or a Zika virus are those that include bases that are complementary to the corresponding base on the target.

Further as used herein, "specificity" of a nucleic acid sequence for a target sequence also encompasses nucleic acids and oligonucleotides having a small number of nucleotides, which may not be complementary to the corresponding nucleotides of the target sequence. Such sequences are still "specific" for the target sequence, as used herein, as long as the extent of deviation from complementarity remains functionally of no consequence. In particular, such a sequence is "specific" for the target sequence as long as it hybridizes effectively to the target sequence but does not hybridize to any sequence that is not a target sequence, under the conditions used in given circumstances.

As used herein, an "amplicon" relates to a double stranded nucleic acid segment having a size and sequence that results from an amplification procedure, such as a PCR. The primer binding sites on the target nucleic acid governs amplicon size. The amplified segment of the target nucleic acid becomes the prevalent product of the amplification procedure after a number of cycles of amplification. The amplified segment can be isolated and analyzed by various methods known in the art, such as pyrosequencing Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve the methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 1. Multiple sequence alignment between West Nile Virus (WNV clone G1, SEQ ID NO:8), Zika clone A1 (SEQ ID NO:9), and three Dengue viruses (DENV4 clone E2, SEQ ID NO:10; DENV2 clone C1, SEQ ID NO:11; and DENV1 clone B1, SEQ ID NO:12).

FIG. 2. Flavi-seq Diagnostic Sequence Read—Target=NS5 (SEQ ID NO: 13-25).

FIG. 3. Flavi-seq Speciation of a Flavivirus Panel.

FIG. 5. Flavi-seq Analysis of Serially Diluted Virus in Urine and Serum.

FIG. 6. Flavi-seq Analysis of Serially Diluted Virus in Mosquito Homogenate.

FIG. 7. Limit of Detection in BioMatrix Analysis.

FIG. 8. Clinical Sample Evaluation—Serum/Plasma/Urine (SEQ ID NO:35-62).

FIG. 9. ADSD Evaluation—Mosquito Sentinel Samples (SEQ ID NO:63).

DESCRIPTION

Figure 4:
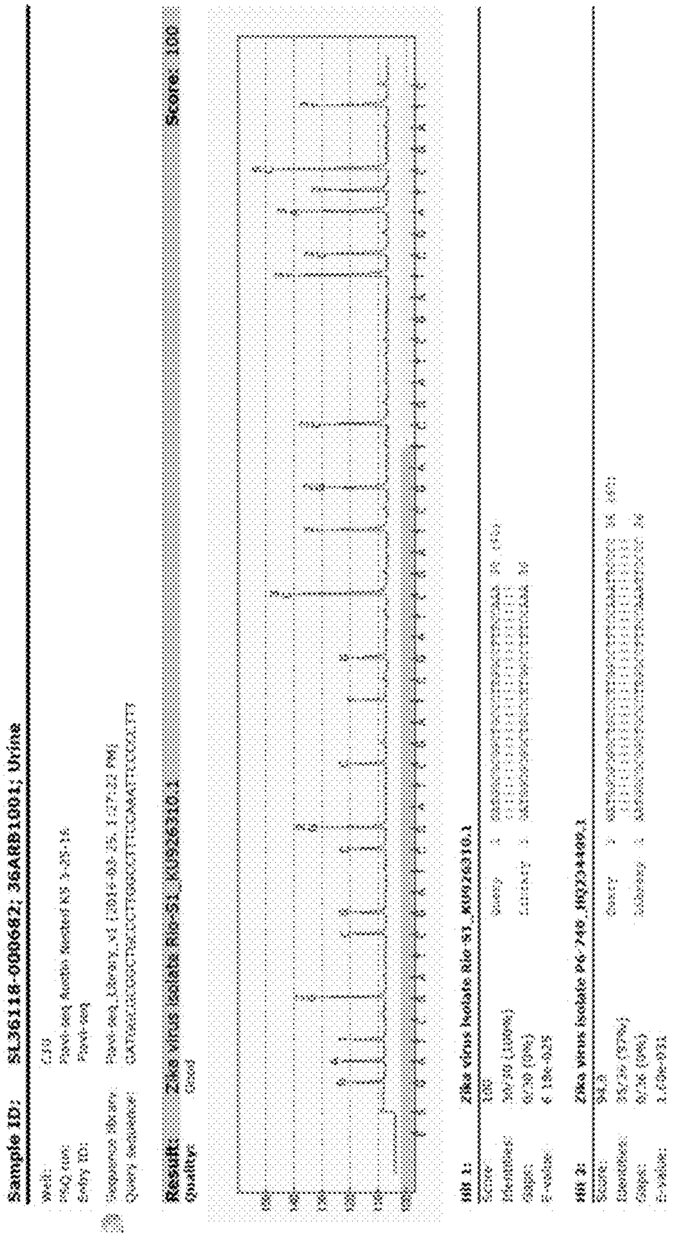
FIG. 4. Flavi-seq Pyrograms of Selected Viruses (SEQ ID NO:26-34).
Figure 4:
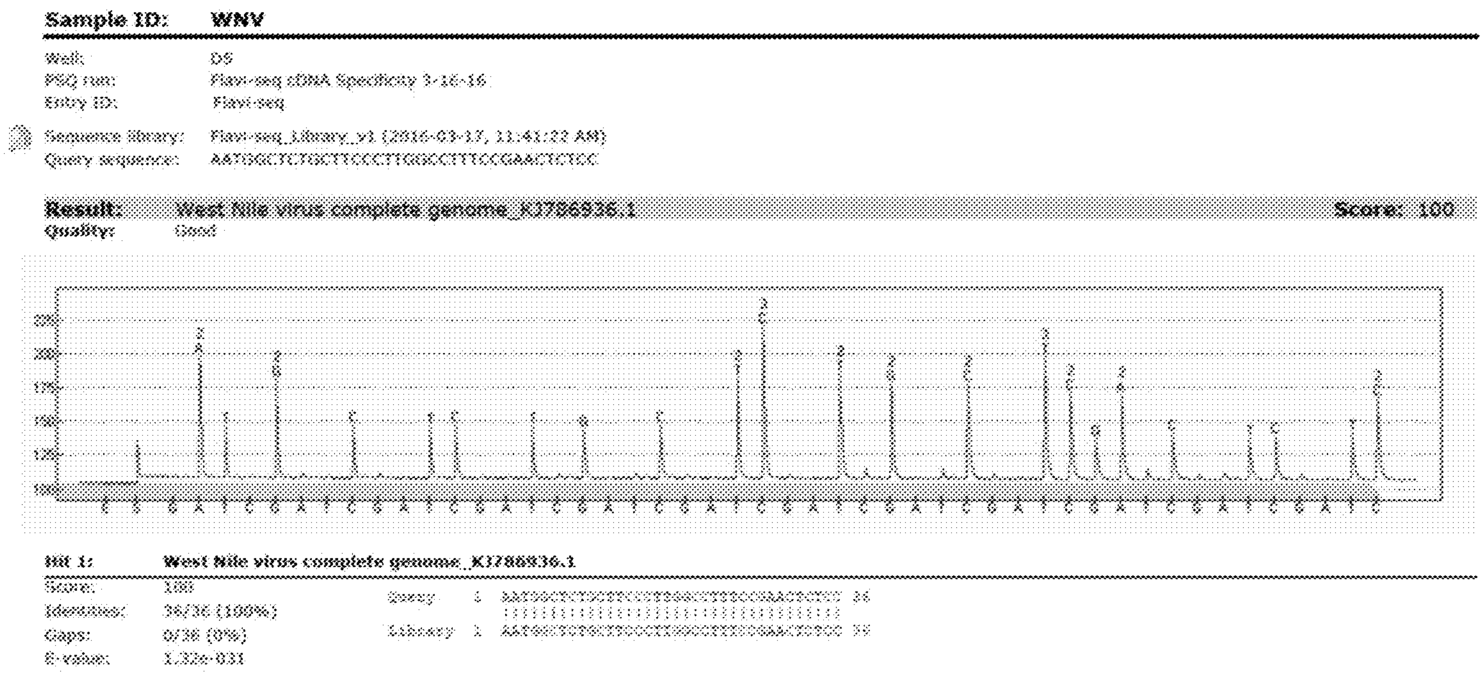
Figure 4:
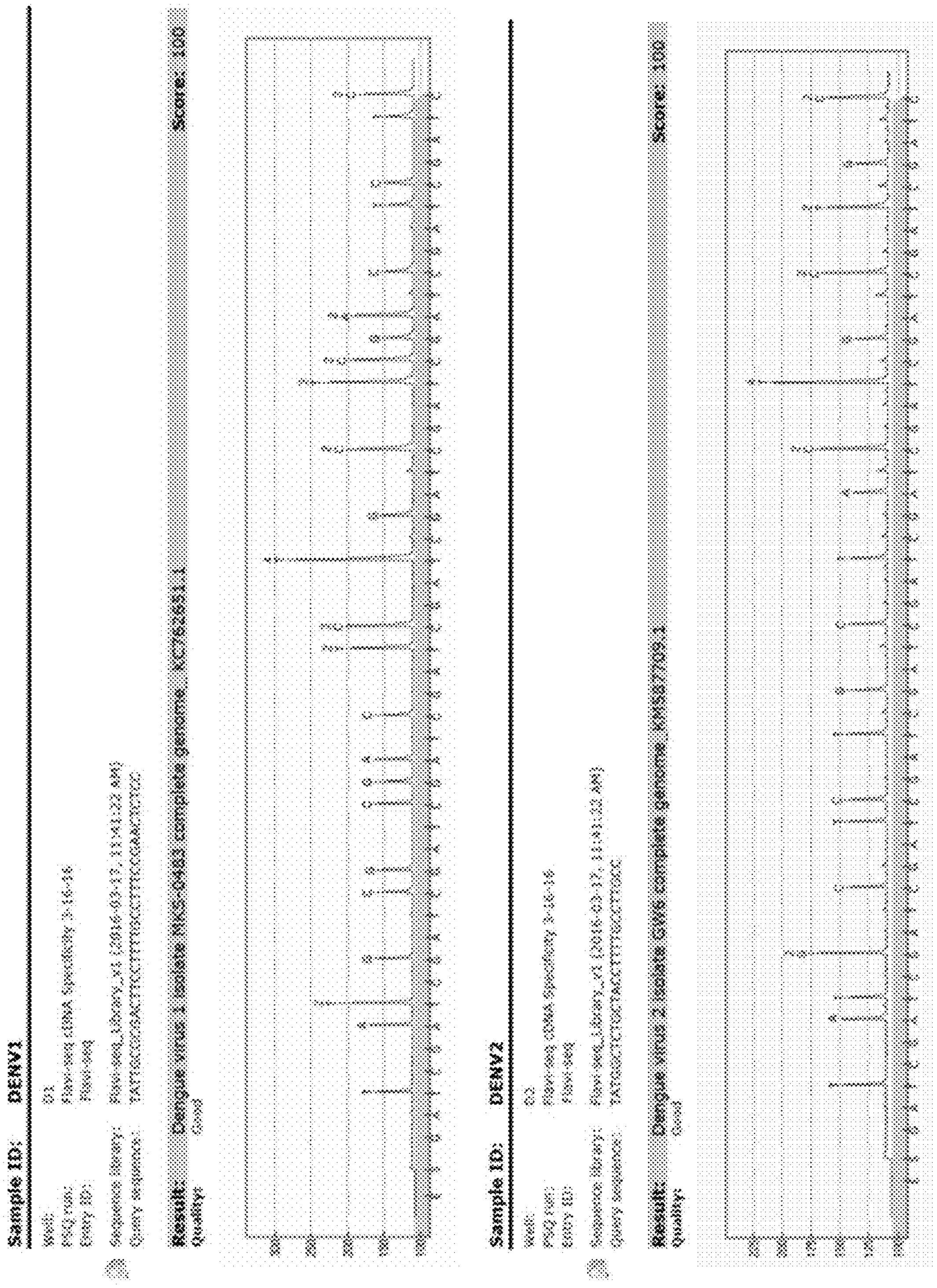
Figure 4:
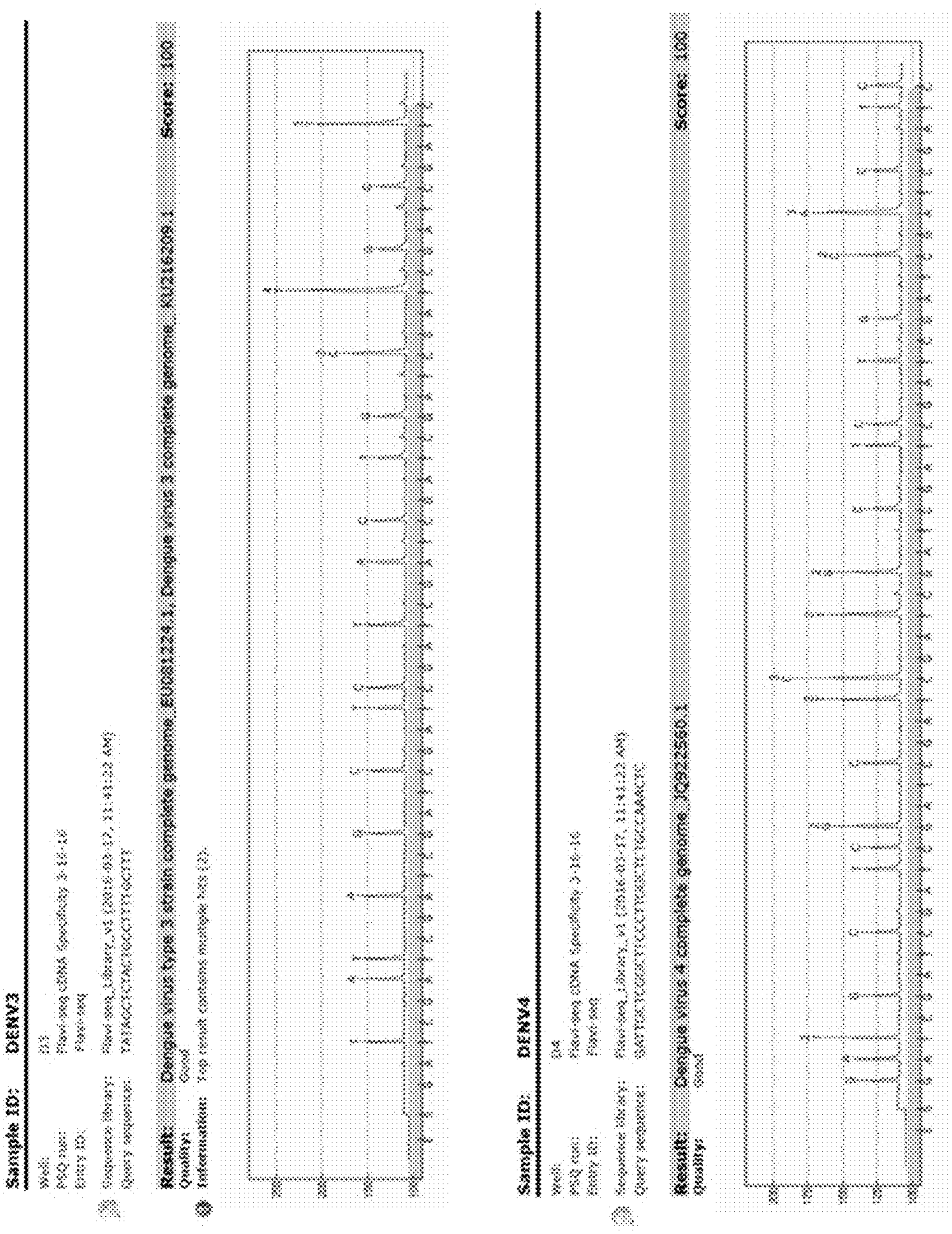

It is important to identify the serotype or subtype of a flavivirus infection in a subject (e.g., a patient). Knowledge of the infecting flavivirus(es) can provide useful guidance to a physician in determining a course of treatment for a disease, condition, or infection. Additionally, an understanding of the geographic and chronological development of a flavivirus infection in a population can influence preventive measures among the members of the population to minimize the spread of the disease or infection. Furthermore, it is useful from a broader perspective to track the incidence and distribution of a flavivirus disease from an epidemiological point of view.

I. FLAVIVIRUS

The genus Flavivirus is a genera of the Flaviviridae family and includes the viral groups of Yellow Fever virus group, Tick-borne encephalitis virus group, Rio Bravo Group, Japanese encephalitis Group, Tyuleniy Group, Ntaya Group, Uganda S Group, Dengue Group, and Modoc Group. Members of the Flavivirus genus may produce a wide variety of disease states, such as fever, arthralgia, rash, hemorrhagic fever, and/or encephalitis. The outcome of infection is influenced by both the virus and host-specific factors, such as age, sex, genetic susceptibility, and/or pre-exposure to the same or a related agent. Some of the various diseases associated with members of the genus Flavivirus are yellow fever, dengue fever, West Nile encephalitis, Japanese encephalitis, and St. Louis encephalitis. For a review of Flaviviruses see Burke and Monath (2001), which is incorporated herein by reference.

Virions of the Flaviviridae generally contain one molecule of a linear positive-sense single stranded RNA genome of approximately 10,000-11,000 nucleotides that replicates in the cytoplasm of an infected cell. Typically the 5' end of the genome has a cap and the 3' end that may or may not have a poly (A) tract. Many members of the genus Flavivirus are transmitted by a vector such as an insect, in many cases the insect is a tick or mosquito.

The viral genome of the Flavivirus genus is translated as a single polyprotein and is subsequently cleaved into mature proteins. The proteins encoded by the virus typically consist of structural and non-structural (NS) proteins. Generally, there are three structural proteins that typically include the envelope protein (E protein) (amino acids 275-787 of GenBank accession number NP_041724, incorporated herein by reference), the core or capsid protein (C) (amino acids 1-92 of GenBank accession number NP_041724), and the pre-membrane protein (preM)(amino acids 105-223 of GenBank accession number NP_041724) (Yamshchikov et al., 2001, incorporated herein by reference). The envelope protein is approximately 496 amino acids with an approximate molecular weight of 50 kDa and is often glycosylated. The core protein is approximately 13 kDa and is rich in arginine and lysine residues. The pre-membrane protein is approximately 10 kDa and is cleaved during or after release of the virus from infected cells. A cleavage product of the prM protein remains associated with the virion and is approximately 8 kDa and is termed the membrane protein (M).

Typically, it is the carboxy terminus of prM that remains associated with the virus particle as the M protein.

Serological comparisons of West Nile virus strains have distinguished four major antigenic subtypes: a group of strains from Africa; strains from Europe and some Asian strains; strains from India; and strains of Kunjin virus from Australasia (Doherty et al., 1968; Hammam et al., 1966; Blackburn et al., 1987; Calisher et al., 1989; Morvan et al., 1990). Subsequently, analyses of nucleotide sequences identified two major genetic lineages, designated I and II, which included some subtypes and which correlated well with the antigenic groupings. Genetic lineage I included European and some African strains, Kunjin virus strains, and Indian strains; lineage II comprised only African strains (Lanctiotti et al., 1999; Jia et al., 1999; Scherret et al., 2001).

Various members of the Flaviviridae family are available through the American Type Culture Collection (Manassas Va.) under the following ATCC numbers: Dengue type 1 (VR-71), Ilheus (VR-73), Japanese encephalitis (VR-74), Murray Valley encephalitis (VR-77), Ntaya (VR-78), St. Louis encephalitis (VR-80), Uganda S (VR-81), West Nile (VR-82), Zika (VR-84), Dengue type 4 (VR-217), Dengue type 2 (VR-222), Japanese encephalitis (VR-343), Dengue type 1 (VR-344), Dengue type 2 (VR-345), Edge hill (VR-377), Entebbe bat (VR-378), Kokobera (VR-379), Stratford (VR-380), Tembusu (VR-381), Dakar bat (VR-382), Ntaya (VR-78), Banzi (VR-414), Modoc (VR-415), Rio Bravo virus (VR-416), Cowbone ridge (VR-417), Bukalasa (VR-418), Montana *myotis* leukoencephalitis (VR-537), Bussuquara (VR-557), Sepik (VR-906), Cowbone ridge (VR-1253), Dengue type 2 (VR-1255), Dengue type 3 (VR-1256), Dengue type 4 (VR-1257), Ilheus (VR-1258), Rio Bravo virus (VR-1263), St. Louis encephalitis (VR-1265), West Nile (VR-1267), Dengue type 4 (VR-1490), West Nile (VR-1507), and West Nile (VR-1510), each of which is incorporated herein by reference.

The genomic sequence of various flavivirus can be found in various nucleic acid sequence databases, such as GenBank. Examples of corresponding sequences, which include the nucleotide sequence of the first and second target region of the NS5 coding region, can be found under the following GenBank accession numbers: West Nile Virus (KJ501270.1), Zika virus (JN860885.1), Dengue 4 (KM190936.1), Dengue 2 (KM587709.1), Dengue 1 (AB189121.1), and Yellow Fever Virus (NC 002031), each of which is incorporated herein by reference as of the filing date of this application.

II. FLAVIVIRUS IDENTIFICATION

Certain embodiments are directed to methods and compositions for amplifying and analyzing a target portion of the NS5 gene. In certain aspects the target portion of flavivirus comprises the nucleic acid sequence corresponding to SEQ ID NO:1 or 2 or a corresponding portion of one or more of GenBank Accession numbers KJ501270.1, JN860885.1, NC_012532.1, KM190936.1, KM587709.1, AB189121.1, NC_002031, AF411835.1, JF415927.1, JF415925.1, JF415919.1, AF098737.1, AF098736.1, AF098735.1, AB479041.1, JN368477.1, JN368476.1, AB488408.1, NC_008604.2, NC_006551.1, NC_000943.1, NC_012534.1, NC_012533.1, KM066945.1, KC481679.1, NC_005062.1, NC_004355.1, KP938507.1, KF751871.1, FJ753287.2, FJ753287.2, NC_003687.1, NC_005064.1, HM055369.1, AF094612.1, and the like, all of which are incorporated herein by reference in its entirety as of the priority date of this and related applications. Oligonucleotide primers (amplification primers or amplimers) can be used to amplify a target region from nucleic acids in a sample. The forward or reverse amplification primer can be modified to assist in isolation and/or sequencing of the target region. In certain instances the forward or reverse amplification primers are coupled to an affinity agent, such as biotin. In certain aspects the forward primer, or a combination of two or more primers, can be 16 to 30 nucleotides in length and comprise or consists of the flavivirus sequence of SEQ ID NO:3, 4, 5, 6, and/or 7, as well as a sequence that varies by 1, 2, 3 or 4 nucleotides from these sequences. If two or more primers are used the primers can be present in equimolar (1:1) concentration or as various molar ratios such as 1:0.9, 1:0.8, 1:0.7, 1:0.6, 1:0.5, 1:0.4, 1:0.3, 1:0.2, or 1:0.1, including all ratios there between. In certain aspects the reverse amplification primer can be 16 to 30 nucleotides in length and comprise or consist of the flavivirus sequence of SEQ ID NO:3 or 6. A third primer can be used as a sequencing primer to sequence the amplified target region. In certain aspects the sequencing primer has or consists of the nucleic acid of SEQ ID NO:7.

The forward and reverse amplification primers were designed after selection of an optimal sequence target region. The primers were synthesized in conjunction with desalting purification of non-modified primers and HPLC purification of any modified or biotinylated primers. Pyrosequencing PCR was carried out using PCR reagents and in conjunction with a thermocycler.

Aspects of the invention include four or more PCR primers, one or more sequencing primers and associated thermocycling protocols targeting a region of the Flaviviridae genome corresponding to the 5' end of the NS5 gene. In certain aspects the target region is used for the purpose of categorizing/speciation of samples. In certain aspects the methods can include using a Qiagen Pyromark ID 96 pyrosequencing platform and associated chemistry, or other sequencing platforms. A larger portion of this region was originally targeted for standard PCR detection amplifying a 269-272 base pair region (Moureau et al, 2008; Vector Borne and Zoonotic Diseases 8:1-11). The system described herein can be called a FlaviSeq system. The FlaviSeq pyrosequencing system recognized the low sensitivity and specificity of the larger PCR target that have now been addressed with novel PCR cycling parameters described herein and a validated pyrosequencing system that diagnostically speciates members of the Flaviviridae genus through a nested PCR amplification step.

In certain embodiments the assay uses cDNA from clinical, mosquito sentinel, or preclinical material; or flavivirus positive PCR amplicons as a template in a nested reaction followed by pyrosequencing PCR. The ability to use nested PCR for flavivirus positive samples enhances sensitivity and offers advantages by preserving irreplaceable stocks of clinical material-derived cDNA as well as the ability to select only positive samples for downstream pyrosequencing analysis thus reducing costs.

In particular examples of the invention, primers were designed using Pyromark Assay Design 2.0 software for SQA analysis. The region selected in the aligned flavivirus genomes was accomplished through multiple sequence analysis of published sequences and evaluation ultimately leading to the selection of a region within the published "pan-flavi" amplimer (Moureau et al, 2008). The designed primers were synthesized by Sigma-Genosys with desalt purification used for the PCR primers and HPLC purification used for biotinylated primers. Pyrosequencing PCR was carried out using Bio-Rad iQSupermix PCR reagents in conjunction with a C1000 thermocycler. Initial validation of the PCR assay was performed using TOPO TA plasmid clones derived from clinical material positive for selected flaviviruses (including Zika (Asian lineage), Dengue virus serotype 1 (DNV1), DNV2, DNV3, DNV4 and West Nile virus).

Subsequent specificity testing was performed with virus negative human sera (negative control) and the same human sera spiked with Zika virus over a 6 log range. Finally, purified stocks of viral lysates were provided by the UTMB viral repository (Dr. R Tesh and T Ksiazek). The specificity panel included 38 distinct viral targets including 33 flavivirus genus members, 3 alphavirus family members and 2 other RNA viruses (Table 1). Among the flaviviruses were 8 contemporary Zika isolates. These samples were previously evaluated by qPCR with TaqMan probe based PCR assays recommended by the CDC or published in the scientific literature.

TABLE 1

| Virus examples | |
|---|---|
| AEDES ALBOPICTUS FLAVI | FLAVIVIRUS |
| ALKHUMRA | FLAVIVIRUS |
| CE TBE | FLAVIVIRUS |
| CELL FUSING AGENT | FLAVIVIRUS |
| CHIKUNGUNYA | ALPHAVIRUS |
| CULEX FLAVI | FLAVIVIRUS - MOSQUITO-SPECIFIC |
| DENV 1 | FLAVIVIRUS |
| DENV2 | FLAVIVIRUS |
| DENV3 H87 | FLAVIVIRUS |
| DENV4 | FLAVIVIRUS |
| DONGGANG | FLAVIVIRUS |
| HCV UTMB 2 | FLAVIVIRUS |
| ILHEUS | FLAVIVIRUS |
| JEV | FLAVIVIRUS |
| KAMATI RIVER | FLAVIVIRUS |
| KFD | FLAVIVIRUS |
| MAYARO | ALPHA VIRUS |
| MURRAY VALLEY ENC | FLAVIVIRUS |
| NANAY | FLAVIVIRUS |
| NOURANE | UNCLASSIFIED |
| OMSK | FLAVIVIRUS |
| O'NYONG NYONG | ALPHAVIRUS |
| POWASSAN | FLAVIVIRUS |
| RSSE | FLAVIVIRUS |
| SPONWENI | FLAVIVIRUS |
| ST. LOUIS ENC | FLAVIVIRUS |
| USUTU | FLAVIVIRUS |
| WNV | FLAVIVIRUS |
| YELLOW FEVER | FLAVIVIRUS |
| ZIKA- NICK V 1-7 EJA MEX P/2 | FLAVIVIRUS |
| ZIKA-NICK V OAK A- 41525 D2-2 | FLAVIVIRUS |
| ZIKA-NICK V OAK A ARD 41662 D2-1 | FLAVIVIRUS |
| ZIKA-NICK V OAK AR 41671 OG-1 | FLAVIVIRUS |
| ZIKA-NICK V FSS 13025 DG-3 | FLAVIVIRUS |
| ZIKA-NICK V ISH 30656 D5-3 | FLAVIVIRUS |
| ZIKA- NICK V PB-7 YO D7-1 | FLAVIVIRUS |
| ZIKA CAMBODIA | FLAVIVIRUS |
| HIV CDNA | RETROVIRIDAE |
| V19 DNA CONTROL | |

Preparation of PCR amplicons for pyrosequencing can be performed using a Qiagen Pyromark Q96 vacuum workstation. In one example, Pyrosequencing was run in SQA mode on the Pyromark ID using Pyromark Gold reagents. Optimal conditions for the sequencing were empirically established and included a cyclic dispensation order of 12 (GCAT) and a final sequencing primer concentration of 0.3 μM. Further validation of the pyrosequencing assay was performed by evaluating clinical material from a cohort of pregnant women providing de-identified sera and/or amniotic fluid. Collectively, the studies with known synthetic and unknown clinical material led to the population of a database of sequences from a variety of clinical and lab-based sources that completes the analysis tools in the invention.

Synthetic sensitivity controls can be included during the validation and evaluation methods. In every case, these validation tests did not identify viral sequences from any negative samples or from samples that contained off target viruses. As expected, 13 of the selected 32 qPCR negative samples revealed low level infections with Zika or Dengue viruses common to the clinical materials being evaluated based on the enhanced sensitivity of the method described herein. The synthetic spiked dilution series showed a lower limit of detection of ~10 genomes/100 μl of clinical material. By comparison, the 136 clinical samples screened by 4 distinct qPCR primer pairs to Zika or other flavivirus targets showed only 65 positives with at least one of the four primer pairs. Considering data from the two CDC recommended primer pairs only revealed a total of 59 positives. Using the optimized FlaviSeq methods on the same clinical samples the inventors found that 129/136 were positive for Zika, 2/136 were positive for Dengue virus serotype 1, and 7 were co-infections of Zika and Dengue virus. This result confirmed there were 70 false negative calls by the two CDC recommended PCR primers. The analyses confirmed 5/136 samples were free from detectable viruses. The synthetic positive and negative controls confirmed the validity of the data set. Importantly, the two DNV-1 single infections were both misidentified as Zika by the qPCR approach (false positives).

Collectively, these results illustrate the utility and enhanced diagnostic and molecular epidemiological value of the FlaviSeq pyrosequencing assay that clearly discriminated between qPCR cross-reactivity of the closely related flavivirus members.

In other embodiments the compositions and methods described herein can be used for sentinel testing of mosquitoes that are being evaluated by many US coastal communities and many international sites to monitor the potential for human infection by positive insects. The FlaviSeq system can provide for discrimination of flaviviruses that are present in mosquito populations in cost effective and high throughput fashion greatly expanding the potential value of these essential programs.

A. Amplification

In certain aspects of the invention a flavivirus target region is prepared by amplification. Amplification of "fragments thereof" refers to production of an amplified nucleic acid containing less than a complete target nucleic acid (e.g., a flavivirus genome or cDNA thereof) or its complement. Such fragments may be produced by amplifying a portion of the target nucleic acid, for example, by using amplification primers that hybridize to, and initiate polymerization from, an internal position of the nucleic acid. Known amplification methods include, for example, transcription-mediated amplification, replicase-mediated amplification, polymerase chain reaction (PCR) amplification, ligase chain reaction (LCR) amplification and strand-displacement amplification (SDA). Replicase-mediated amplification uses self-replicating RNA molecules, and a replicase such as QB-replicase (e.g., U.S. Pat. No. 4,786,600; PCT WO 90/14439, each of which is incorporated herein by reference). PCR amplification is well known and uses a DNA polymerase, primers and thermal cycling to synthesize multiple copies of the two complementary strands of DNA (e.g., U.S. Pat. Nos. 4,683,195, 4,683,202, and 4,800,159, each of which is incorporated herein by reference). LCR amplification uses at least four separate oligonucleotides to amplify a target and its complementary strand by using multiple cycles of hybridization, ligation, and denaturation (see EP Patent Application 0 320 308, which is incorporated herein by reference). SDA is a method in which a primer contains a recognition site for a restriction endonuclease such that the endonuclease will nick one strand of a hemi-modified DNA duplex that includes the target sequence, followed by amplification in a series of primer extension and strand displacement steps (see U.S. Pat. No. 5,422,252, which is incorporated herein by reference). It will be apparent to one skilled in the art that the amplification oligonucleotides disclosed herein are readily applicable to other amplification methods that use primer extension.

In certain aspects polymerase chain reaction (PCR) is used to amplify an flavivirus target region. As used herein, the term "PCR" is well known. Generally, PCR includes the steps of: (a) obtaining target nucleic acid molecules from a sample; (b) adding an aqueous solution including an enzyme, a buffer, dNTPs, and oligonucleotide primers to the sample; (c) amplifying the target DNA molecules by thermal cycling using two or more cycling steps (denaturation, annealing, and/or extension cycles) of the resultant mixture; and (d) detecting amplified nucleic acids, typically DNAs. The PCR may be performed in a polypropylene tube, a multi-well plate, an emulsion bubble, a fluidics chamber or a silicon-based micro PCR chip.

The present invention also provides an flavivirus assay kit including amplification primers for typing flavivirus. A kit may include the primers, a PCR solution, a buffer, an enzyme, and the like.

B. Sequencing

Once an amplicon of the target region is obtained, the sequence of the amplicon can be determined. A variety of methods are known in the art for determining the sequence of a nucleic acid that include, but are not limited to, pyrosequencing, chain termination sequencing, adaptor ligation sequencing (massively parallel signature sequencing (MPSS)), and reversible dye-terminator sequencing (Illumina Sequencing).

In certain aspects an amplicon is sequenced using pyrosequencing. Pyrosequencing can provide increased speed and identification of exact sequence variation. Pyrosequencing is a sequencing technology based on the iterative incorporation of specific nucleotides during primer-directed polymerase extension, providing real time sequence information. Pyrosequencing can also reduce costs of each assay.

Primers can be synthesized by Sigma-Genosys, or similar company providing synthesis services, with desalting purification used for the reverse amplification primer and the sequencing primer and HPLC purification used for biotinylated forward amplification primer.

Pyrosequencing PCR can be performed on a Qiagen Pyromark™ ID 96 pyrosequencing platform (Qiagen) using a final sequencing primer concentration of 0.3 μM and cyclic dispensation of 20 (GCAT). The master mix (per sample) includes 12.5 μl Bio-Rad Supermix (2×); 1.0 μl Forward primer (5 μM); 1.0 μl Reverse primer (5 μM); and water to volume. The template is amplified in 25 μl total reaction volume using PCR protocol defined as 95 C for 1:30; 95 C 0:15, 60 C 1:00, x 50; 72 C 5:00; and 4 C indefinite hold. The pyrosequencing PCR can use Bio-Rad iQSupermix PCR in conjunction with a C1000 thermocycler but other combinations could be used as well.

Preparation of the PCR amplicons for pyrosequencing can be performed using a Qiagen Pyromark Q96 vacuum workstation. Pyrosequencing was run in SQA mode on the Pyromark ID using Pyromark Gold reagents. Optimal conditions for the sequencing were empirically established and included an empirically derived cyclic dispensation order of 20 (GCAT) and a final sequencing primer concentration of 0.3 μM.

As described herein, sequence information provides reliable data for flavivirus genotyping applications. However, standard methods used to assess discriminatory regions of viral genomes can be time-consuming, may require species-specific probes or gel electrophoresis, or are susceptible to the presence of unknown mutations that alter the outcomes of assays (e.g., primer hybridization). Tracking outbreaks or the emergence of genetically drifted species is of critical importance to fields of infection control and viral pathology.

III. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

PCR/Pyromark Pyrosequencing Assay to Identify the Presence of Viral Nucleic Acid and to Speciate Flaviviruses in Biological Samples Sample extraction can be done on a Roche *Magna* Pure 96 platform using Cellular Large volume RNA extraction kits (05467535001). Primary samples are lysed using *Magna* Pure 96 Exteral Lysis Buffer IVD (06374913001). cDNA is synthesized using Bio-Rad iscript reagents in accordance with the manufacturer. This assay can be used as nested PCR or pyrosequencing PCR alone.

PCR: Bio-Rad c1000 conventional or CFX96 real-time instrument. Pyrosequencing Primers: 5'-3'

PCR Round 1:

PCR Screen—KS thermocycling; PF1S: TGY-RTB-TAY-AAC-ATG-ATG-GG, PF2R-bis: GTG-TCC-CAI-CCN-GCN-GTR-TC, Moureau et al., 2007.

Thermocycling: KS (1) 95.0 C for 1:30; (2) 95.0 C for 0:30, (3) 48.0 C for 0:30—Increment temperature by 0.9 C per cycle and Slow Ramp Rate to 1.3 C per second; (4) 72.0 C for 0:30—Slow Ramp Rate to 1.6 C per second; (5) GOTO 2, 7 more times; (6) 95.0 C for 0:15—Slow Ramp Rate to 0.9 C per second; (7) 56.0 C for 0:20—Slow Ramp Rate to 1.1 C per second; (8) 72.0 C for 0:20—+Plate Read, Slow Ramp Rate to 0.9 C per second; (9) GOTO 6, 39 more times; (10) 72.0 C for 2:00; (11) Melt Curve 65.0 to 95.0 C—increment 0.2 C, 0:05+Plate Read; and END.

Alternative Thermocycling procedure for Round 1: (1) 95.0 C for 1:30; (2) 94.0 C for 0:15; (3) 50.0 C for 0:30; (4) 72.0 C for 0:45—+Plate Read; (5) GOTO 2, 49 more times; (6) 72.0 C for 2:00; (7) Melt Curve 70.0 to 95.0 C, increment 0.2 C, 0:05+Plate Read; and END. Note: Plate reads and Melt curve are only necessary when employing real-time PCR cycling.

Pyrosequencing: Nested Assay

Based on amplification of the first-round PCR screen amplimer or primary on cDNA template. F: Biotin-GTGTC-TACAACATGATGGGAAAGAG (SEQ ID NO:5); R: CTCCCAGCCACATGTACCA (SEQ ID NO:6); and Sequencing primer CCAGCCACATGTACCA (SEQ ID NO:7). Note: Final sequencing primer concentration=0.3 μM. Thermocycling—Round 1 for cDNA template or Round 2 for nested reaction: (1) 95.0 C for 3:00; (2) 95.0 C for 0:30; (3) 58.4 C for 0:30; (4) 72.0 C for 0:30—+Plate Read; (5) GOTO 2, 49 more times; (6) 72.0 C for 2:00; (7) Melt Curve 77.0 to 86.0 C, increment 0.2 C, 0:05+Plate Read; and END. Note: Plate reads and Melt curve are only necessary when employing real-time PCR cycling.

Pyrosequencing amplicon clean-up and preparation is carried out using the manufacturer's (QIAGEN) protocol. Pyrosequencing is carried out using a PyroMark 96 ID system using the on board software in SQA mode.

Cyclic Dispensation: 12 (GATC)

Data are analyzed using Identifier software (QIAGEN) using a custom library of reference sequences. Reports are then exported via PDF reports from Identifier.

Example 2

Mosquito BioMatrix Testing

Materials and Methods

Pools of wild-caught mosquitoes were processed to homogenate using a VecTest kit (Medical Analysis Systems Inc., Camarillo, Calif.) according to the manufacturer's protocol. Homogenates were pre-screened for the presence of flaviviruses to ensure negative background materials for subsequent evaluations. Flavivirus-negative mosquito homogenates were used to create simulated flavivirus positive samples for Flavi-seq evaluation in this biomatrix. Stock viruses consisting of 6 Zika isolates (representing the African (2), Asian (2) and Americas (3 including a contemporary isolate) genetic lineages), West Nile virus and Dengue viruses of serotype 1, 2, 3 and 4 were spiked into mosquito homogenates and then subjected to ten-fold serial dilution. The resulting mosquito homogenate/flavivirus dilution mixtures were extracted using a MagnaPure 96 (Roche, Indianapolis, Ind.) in combination with a MagnaPure 96 cellular RNA large volume kit for RNA isolation. The purified RNA was converted into cDNA (iScript, Bio-Rad) and used as input template for Flavi-seq evaluation (Slide 9 in the accompanying power point file). Quality assessment of RNA extracted from each mosquito homogenate was completed using qPCR for the mosquito 12s housekeeping gene (Slide 12).

Results

Flavi-Seq Limit of Detection (LOD) Estimations.

Because of the broad range applicability of the Flavi-seq assay, determining the LOD for each individual flavivirus was not completed for each biomatrix. LOD limits were determined using 3 Zika virus isolates of Americas genetic lineage currently in circulation. Serial dilutions of known viral stocks were spiked into multi-donor pooled human serum, human urine and mosquito homogenate biomatrices that were found to be negative for any flavivirus genetic material. RNA was extracted, cDNA created and then subjected to optimal single or nested PCRs to create material for analysis in the Flavi-seq system (see Flavi-seq assay description). The results are summarized in the table below (also see FIG. 7).

| LOD (genome copies) | Flavi-seq (cDNA) | Flavi-seq (Nested) |
|---|---|---|
| Serum | 700 | BLD |
| Urine | 469 | BLD |
| Mosquito | 850 | N/A |

BLD: below level of qPCR detection.

BLD: below level of qPCR detection.

Mosquito Sentineling Results:

As part of the SE Texas effort to screen mosquitoes for local spread of Zika and other flaviviruses, several monthly mosquito pool sampling efforts were supported using standard PCR approaches. These same samples were also screened using Flavi-seq. This approach identified a mosquito-specific flavivirus in a single mosquito pool sample. This result along with the spike study demonstrated the ability of Flavi-seq to surveil both human clinical material and insect homogenates for a broad range of flaviviruses within these and likely other biomatricies. (FIG. 6 and FIG. 9)

Additional Clinical Sample Data:

De-identified clinical samples derived from serum, urine or plasma from patients located in Bolivia, Colombia and Honduras were evaluated using Flavi-seq and compared to standard qPCR for Zika virus. Concordance analysis between these methods (FIG. 8) illustrated the utility and value of Flavi-seq over standard qPCR approaches. The detection of contemporary Americas Zika virus in these clinical samples demonstrates the applicability as well as capability of the Flavi-seq assay to identify emerging geographically distinct flaviviruses within human biological material including several that were not detected by the standard approaches. Further, Flavi-seq identified two distinct Dengue serotypes (DNV1 and DNV4) within this sample cohort.

Flavi-Seq Significance:

The ability to detect and speciate multiple flaviviruses including those that cause significant impacts to human health are demonstrated in the provided data. In silico analyses, as indicated using a multiple sequence alignment specific to the Flavi-seq assay (FIG. 2) confirm the theoretical potential for complete identification of viral members of this family. These alignments illustrate sequences from Zika virus (4 African, 2 Asian and 1 Americas), West Nile virus, Dengue virus serotypes 1, 2, 3 and 4 and a mosquito-specific flavivirus (Cell-fusing agent). The Cell-fusing agent virus was detected in the Harris county mosquito pool mentioned above.

The invention claimed is:

1. A method of identifying flavivirus in a sample comprising:

(a) isolating a nucleic acid segment of a flavivirus NS5 coding region corresponding to a nucleic acid segment consisting of the nucleic acid sequence of SEQ ID NO:1;

(b) amplifying a subsequence of the isolated nucleic segment; and (c) determining the nucleotide sequence of a portion of the amplified subsequence, wherein the nucleotide sequence identifies a flavivirus in the sample.

2. The method of claim 1, wherein isolating in step (a) comprising amplifying nucleic acids in a sample using amplimers having nucleotide sequences consisting of SEQ ID NO:3 or SEQ ID NO:4.

3. The method of claim 1, wherein amplifying of the subsequence comprises using amplimers having a nucleotide sequence consisting of SEQ ID NO:5 or SEQ ID NO:6.

4. The method of claim 1, wherein sequencing of the subsequence nucleic acid uses a sequencing primer having a nucleotide sequence consisting of SEQ ID NO:7.

5. The method of claim 1, wherein the corresponding nucleic acid segment has a nucleotide sequence of SEQ ID NO:2.

6. The method of claim 1, wherein the subsequence segment corresponds to nucleotide 3 to 94 of SEQ ID NO:1 or 2.

7. The method of claim 1, wherein more than one flavivirus is present in the sample.

8. The method of claim 7, wherein a plurality of amplified subsequence nucleic acid segments are sequenced.

9. The method of claim 1, wherein the amplified subsequence nucleic acid segment is an amplicon.

10. The method of claim 9, wherein the amplicon is a PCR amplicon.

11. The method of claim 1, wherein the amplified subsequence nucleotide sequence is determined by pyrosequencing.

12. The method of claim 7, wherein the sample is a semen, amniotic fluid, blood, urine, lymph, sputum, saliva, or tissue sample.

13. The method of claim 7, wherein the sample is from a human, an insect, or an animal.

14. The method of claim 13, wherein the insect sample is a tick or mosquito sample.

15. A flavivirus profiling kit comprising (i) oligonucleotides consisting of nucleic acid sequence of SEQ ID NO:3, SEQ ID NO:4, SEQ ID NO:5, SEQ ID NO:6, and SEQ ID NO:7; and amplification reagents.

16. Amplification primers having a nucleotide sequence consisting of SEQ ID NO: 3, SEQ ID NO:4, SEQ ID NO:5, or SEQ ID NO:6.

* * * * *